United States Patent
Ohmachi et al.

(10) Patent No.: US 7,090,869 B2
(45) Date of Patent: Aug. 15, 2006

(54) METHOD FOR PRODUCING PREPARATION CONTAINING BIOACTIVE SUBSTANCE

(75) Inventors: Yoshihiro Ohmachi, Osaka (JP); Masafumi Misaki, Takarazuka (JP); Shigeyuki Takada, Nishinomiya (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 118 days.

(21) Appl. No.: 10/433,156

(22) PCT Filed: Nov. 29, 2001

(86) PCT No.: PCT/JP01/10416

§ 371 (c)(1),
(2), (4) Date: May 30, 2003

(87) PCT Pub. No.: WO02/43709

PCT Pub. Date: Jun. 6, 2002

(65) Prior Publication Data

US 2004/0018240 A1    Jan. 29, 2004

(30) Foreign Application Priority Data

Dec. 1, 2000    (JP) .............................. 2000-367183

(51) Int. Cl.
*A61K 9/14*    (2006.01)
(52) U.S. Cl. ............. 424/489; 424/468; 424/486; 424/44; 424/45; 426/425; 264/5
(58) Field of Classification Search ............ 424/45, 424/468, 486, 489, 44; 426/425; 264/5
See application file for complete search history.

(56) References Cited

U.S. PATENT DOCUMENTS

| | | | |
|---|---|---|---|
| 4,675,189 A | 6/1987 | Kent et al. | 424/490 |
| 4,978,752 A * | 12/1990 | Maeda et al. | 540/222 |
| 5,232,707 A * | 8/1993 | Lokensgard | 424/490 |
| 5,287,632 A * | 2/1994 | Heit et al. | 34/341 |
| 5,766,637 A | 6/1998 | Shine et al. | |
| 5,773,032 A * | 6/1998 | Engel et al. | 424/501 |
| 6,391,452 B1 * | 5/2002 | Antonsen et al. | 428/402.2 |
| 6,403,672 B1 * | 6/2002 | Randolph et al. | 522/79 |
| 6,514,518 B1 * | 2/2003 | Monkhouse et al. | 424/427 |
| 6,613,358 B1 * | 9/2003 | Randolph et al. | 424/489 |
| 6,620,351 B1 * | 9/2003 | Gupta et al. | 264/7 |
| 2003/0072716 A1 * | 4/2003 | Poovathinthodiyil et al. | 424/43 |
| 2003/0161957 A1 * | 8/2003 | Colombo et al. | 427/372.2 |
| 2004/0121008 A1 * | 6/2004 | Shiraishi et al. | 424/468 |

FOREIGN PATENT DOCUMENTS

| | | |
|---|---|---|
| EP | 0 601 799 | 6/1994 |
| EP | 0 761 213 | 3/1997 |
| WO | 96/07399 | 3/1996 |
| WO | 97/01331 | 1/1997 |
| WO | 99/48519 | 9/1999 |

OTHER PUBLICATIONS

Falk (Pharmaceutical Research 15(8), 1233-37, 1998.*
Kaiser C. S., Die Pharmazie, (Dec. 2001) 56 (12) 907-26.*
Karlsson L., Journal of pharmaceutical and biomedical analysis, (Feb. 1997) 15 (5) 601-11.*
CRC Handbook of Chemistry and Physics, internet version 2005, D.R. Lide, ed., www.hbcpnetbasd.com, CRC Press, Boca Raton, Fl, table 1-34.*

* cited by examiner

*Primary Examiner*—David Lukton
(74) *Attorney, Agent, or Firm*—Wenderoth, Lind & Ponack, L.L.P.

(57) ABSTRACT

A method for producing a preparation containing a bioactive substance, characterized in that it comprises forming a solid material containing the bioactive substance and a polymer, and contacting the solid material with a high pressure gas. The method allows the production of a preparation which is suppressed in excessive initial release of the bioactive substance immediately after the administration thereof, is capable of releasing a predetermined amount of the bioactive substance over a long period of time, and is extremely reduced in the deterioration of the bioactive substance and in the amount of a residual organic solvent.

18 Claims, 1 Drawing Sheet

METHOD FOR PRODUCING PREPARATION CONTAINING BIOACTIVE SUBSTANCE

This application is a 371 of PCT/JP01/10416, filed Nov. 29, 2001, which claims priority to Japanese application 2000-367183, filed Dec. 1, 2000.

TECHNICAL FIELD

The present invention relates to a method for producing a preparation containing a bioactive substance. More specifically, the present invention relates to a method for producing a preparation comprising a bioactive substance, which is unstable to heat or solvents, and a polymer.

BACKGROUND ART

Peptidic or non-peptidic bioactive substances are known to exhibit various pharmacological activities in a living body, and the application thereof as medicaments have been attempted. However, it is required to administer these bioactive substances frequently since their half-life in a living body is generally short. Then, physical burden of patients due to administration by injection cannot be ignored. For example, growth hormone, a representative hormone which is originally produced and secreted in the anterior portion of the pituitary gland, is a bioactive peptide having widely diverse physiological activities such as, in addition to promotion of growth in the body, metabolism of saccharides and lipids, anabolism of proteins, cell proliferation and differentiation, and the like. At present, growth hormone is produced on a large scale by *Escherichia coli* using genetic recombination technology, and put to medicinal use clinically and worldwide. However, it is required to administer growth hormone frequently in order to maintain an effective blood level because of its short biological half-life. Especially, in the case of pituitary dwarfism, a daily subcutaneous administration to infants or young patients over a long period of time ranging from a few months to 10 years or more is actually taken place.

In order to deal with problems inherent in such bioactive substances, various drug delivery systems have been studied. For example, a sustained-release agent that provides sustained-release of a bioactive peptide over a long period of time has been studied. JP 8-217691 A (WO96/07399) discloses a method for producing a sustained-release preparation comprising a water-insoluble or poorly water soluble polyvalent metal salt of a water-soluble peptidic bioactive substance, which is formed by an aqueous solution of zinc chloride, etc., and a biodegradable polymer.

Further, for a sustained-release preparation using a biodegradable polymer, it is desired to maintain the activity of a bioactive substance with suppressing the initial release of a bioactive substance, in particular, release of the excess amount within one day, and to control the release of the bioactive substance arbitrarily over a long period of time. Regarding this problem, JP 11-322631 A discloses a method for producing a sustained-release preparation comprising adding a water-miscible organic solvent and/or a volatile salt to an aqueous solution of a bioactive peptide, followed by lyophilizing to obtain a bioactive peptide powder, dispersing the powder in a solution of a biodegradable polymer in an organic solvent, and removing the organic solvent. Furthermore, JP 9-132524 A discloses a method for producing sustained-release microcapsules comprising a bioactive substance and a biodegradable polymer which comprises, after forming microcapsules, heat-drying the microcapsules at a temperature of not less than the glass transition temperature of the biodegradable polymer for about 24 to 120 hours. These are methods for producing a sustained-release preparation containing very little residual organic solvent and having very superior clinical properties as medicaments.

OBJECTS OF THE INVENTION

However, according to the solvent-removing procedures in the above-mentioned production methods, since it takes long period of time for removing the solvent, there is still room for improvement in view of the production costs for the industrial application.

On the other hand, as a procedure for removing a solvent that remains in a component (e.g., polymer) used for formulating a preparation of a medicament, heat drying method, vacuum drying method and flash drying with dried gas have been known. However, in these procedures, when a substance has strong affinity for a solvent and is unstable to heat, the removal of the solvent tends to be insufficient or, in some cases, the substance is decomposed. Furthermore, in these procedures, when the boiling point of a solvent to be removed is high, the properties of a preparation obtained may be deteriorated.

SUMMARY OF THE INVENTION

The present inventors have studied intensively to solve the above-mentioned problems and unexpectedly found that, in a method for producing a sustained-release preparation comprising a bioactive substance and a biodegradable polymer, a sustained-release preparation having superior clinical properties as a medicament, in which excess initial release of the bioactive substance immediately after administration is markedly suppressed, a constant amount of the bioactive substance is being released from immediately after administration over a long period of time and very little residual organic solvent is contained therein, can be obtained by, after forming a solid material, contacting the solid material with high-pressure gas for about 10 minutes to about 12 hours. The present invention has been completed based on these findings.

That is, the present invention provides:

(1) A method for producing a preparation containing a bioactive substance, which comprises forming a solid material containing the bioactive substance and a polymer, and contacting the solid material with high-pressure gas;

(2) The method according to the above (1), wherein the bioactive substance is that being unstable to heat or solvents;

(3) The method according to the above (1), wherein the bioactive substance is a bioactive peptide having a molecular weight of about 2,000 to about 500,000;

(4) The method according to the above (1), wherein the bioactive substance is a bioactive peptide having a molecular weight of about 5,000 to about 500,000;

(5) The method according to the above (4), wherein the bioactive substance is human growth hormone;

(6) The method according to the above (1), wherein the bioactive substance is a non-peptidic compound;

(7) The method according to the above (6), wherein the non-peptidic compound is a compound having an oxygen atom in the molecule;

(8) The method according to the above (6), wherein the non-peptidic compound is a compound having an ether bond or a carbonyl group;

(9) The method according to the above (6), wherein the non-peptide compound is a compound represented by the formula (I):

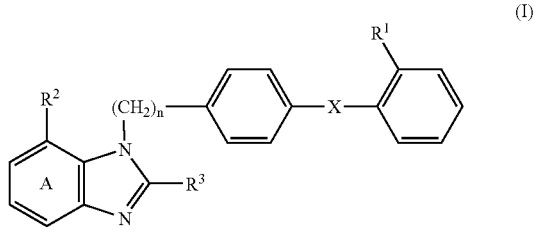

wherein R¹ represents a group capable of forming an anion or a group which may be converted into said group, X represents that the phenylene group and the phenyl group are linked directly or via a spacer of an atomic chain having two or less atom(s), n represents an integer of 1 or 2, ring A represents a benzene ring which may be further substituted, R² represents a group capable of forming an anion or a group which may be converted into said group, R³ represents a hydrocarbon residue which may link via a heteroatom and may be substituted, or a salt thereof;

(10) The method according to the above (6), wherein the non-peptidic compound is losartan, eprosartan, candesartan cilexetil, candesartan, valsartan, telmisartan, irbesartan, tasosartan or olmesartan;

(11) The method according to the above (6), wherein the non-peptide compound is candesartan;

(12) The method according to the above (1), wherein the polymer is biodegradable;

(13) The method according to the above (12), wherein the biodegradable polymer is a homopolymer or a copolymer of α-hydroxycarboxylic acids, or a mixture thereof;

(14) The method according to the above (13), wherein the biodegradable polymer is a homopolymer or a copolymer of lactic acid/glycolic acid having a composition ratio of lactic acid/glycolic acid of about 100/0 to about 40/60 mol %;

(15) The method according to the above (13), wherein the biodegradable polymer is a homopolymer of lactic acid;

(16) The method according to the above (12), wherein the weight-average molecular weight of the biodegradable polymer is about 3,000 to about 50,000;

(17) The method according to the above (1), wherein the solid material is contacted with high-pressure gas at a temperature range of about +20° C. to about −60° C. based on the glass transition temperature of the polymer;

(18) The method according to the above (17), wherein the solid material is contacted with high-pressure gas at a temperature range of about +0° C. to about −40° C. based on the glass transition temperature of the polymer;

(19) The method according to the above (1), wherein the period for contacting the solid material with high-pressure gas is about 5 minutes to about 48 hours;

(20) The method according to the above (19), wherein the period for contacting the solid material with high-pressure gas is about 10 minutes to about 12 hours;

(21) The method according to the above (1), wherein the high-pressure gas is inert to the bioactive substance and polymer;

(22) The method according to the above (21), wherein the high-pressure gas is carbon dioxide;

(23) The method according to the above (1), wherein the pressure of the high-pressure gas is about 1 MPa to about 7 MPa;

(24) The method according to the above (23), wherein the pressure of the high-pressure gas is about 1 MPa to about 4 MPa;

(25) The method according to the above (23), wherein the preparation is sustained-release microcapsules;

(26) The method according to the above (25), wherein the sustained-release microcapsules are obtained by drying-in-water method;

(27) A preparation obtained by the method according to the above (1);

(28) Sustained-release microcapsules obtained by the method according to the above (25);

(29) An injectable preparation comprising the sustained-release microcapsules according to the above (28);

(30) A method for suppressing the initial release of a bioactive substance, which comprises forming a solid material containing said bioactive substance and a polymer, and contacting the solid material with high-pressure gas; and

(31) A method for suppressing the denaturation of a bioactive substance, which comprises forming a solid material containing said bioactive substance and a polymer, and contacting the solid material with high-pressure gas.

Figure 1:
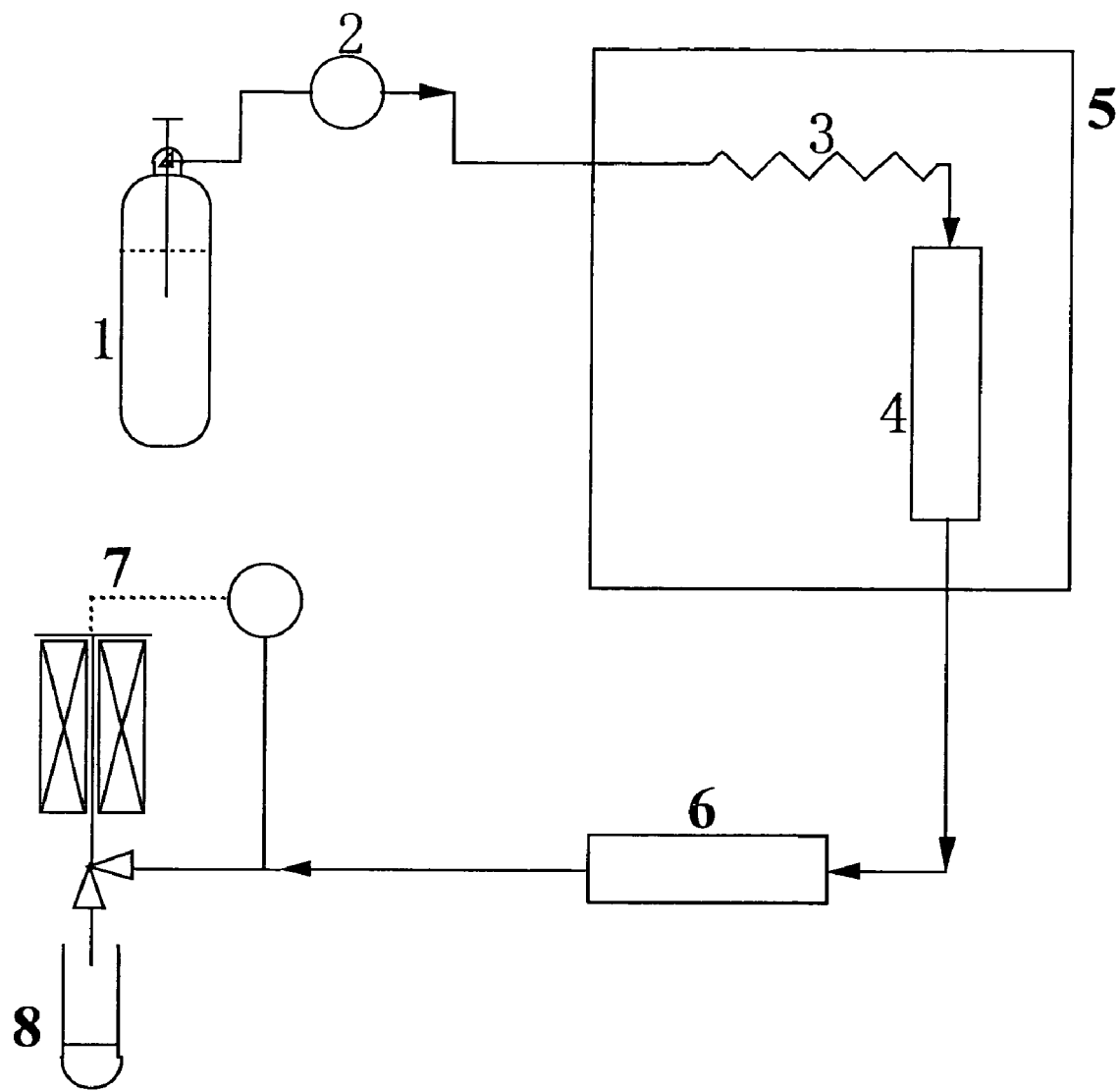
FIG. 1 is a schematic drawing of a solvent-removing apparatus using carbon dioxide in a high-pressure gaseous state.

Each number in the drawing has the following meaning.

1: liquefied carbon dioxide bomb, 2: $CO_2$ delivery pump, 3: heat exchanger, 4: extraction vessel, 5: thermostat, 6: detector, 7: automatic pressure regulating valve, 8: recovery vessel.

DETAILED DESCRIPTION OF THE INVENTION

The bioactive substance used in the present invention includes various drugs, which have useful physiological activities for animals and plants and can be used as an agrochemical or an animal drug, or can be used clinically. As the bioactive substance used in the present invention, a bioactive substance being unstable to heat or solvents is preferred. The bioactive substance being unstable to heat or solvents used herein means a bioactive substance that is decomposed, metabolized, inactivated or denatured in a production step which involves heating or contact with an organic solvent, such as emulsification, removing of a solvent or drying. The agrochemical includes, for example, control agents for pests, control agents for plant diseases, herbicides, plant growth regulators, fertilizers and the like, and the animal drug includes, for example, antibacterial agents, vitamin preparations, hormone preparations, vaccines, additives for fishery products, insecticide and disinfectant preparations, drugs for pets and the like. For an ideal agrochemical or animal drug, which is safe and environment-friendly, reduction of residual solvents is important. Examples of various drugs those can be used clinically include, and are not specifically limited, peptidic compounds having physiological activities, as well as antibiotics, antifungal agents, antihyperlipidemic agents, antitumor agents, antipyretic agents, analgesic agents, antiinflammatory agents, antitussive and expectorant agents, sedatives, muscle relaxants, antiepileptics, antiulcer agents, antidepressants, antiallergic agents, cardiotonics, antiarrhythmic agents, vasodilators, hypotensive diuretics, antidiabetic agents, anticoagulants, hemostatic agents, antiplatelet agents, antituberculous agent, hormones, antinarcotics, bone resorption-suppressing agents, osteogenesis-accelerating agents, and neovascularization suppressing agents. Of these, a peptidic or non-peptidic bioactive substance that produces a dimer, a polymer or related substances such as an oxidized substances, deamidated substances, and the like by heat, or a peptidic or non-peptidic bioactive substance that produces a reaction product with a biodegradable polymer, is preferably used in the present invention.

The bioactive peptide in the present invention includes various peptides or proteins, which have physiological activities useful for mammals and can be used clinically. As the "bioactive peptide", that having a molecular weight (as monomers) of, for example, about 200 to 500,000, preferably molecular weight of about 2,000 to 500,000, is generally used. More preferably, a peptide having a molecular weight of 5,000 to about 500,000 is used.

The typical activity of the bioactive peptide includes hormone activities. The bioactive peptide may be any of natural substances, synthesized substances and semi-synthesized substances, or may be derivatives or related substances thereof. The functional mechanism of the bioactive peptide may be either of agonistic and antagonistic.

As the bioactive peptide in the present invention, there can be used peptide hormones, cytokines, peptide nerve transmitter substances, hematopoietic factors, various growth factors, enzymes, polypeptide antibiotics, analgetic peptides, vaccines, and the like.

As the peptide hormones, there can be used insulin, somatostatin, somatostatin derivatives (Sandostatin; see U.S. Pat. Nos. 4,087,390, 4,093,574, 4,100,117 and 4,253,998), growth hormones (GH), sodium diuretic peptides, gastrin, prolactin, adrenocorticotropic hormone (ACTH), ACTH derivatives (e.g., ebiratide, etc.), melanocyte-stimulating hormone (MSH), thyroid hormone-releasing hormone (TRH) and salts and derivatives thereof (see JP 50-121273 A and JP 52-116465 A), thyroid-stimulating hormone (TSH), luteinizing hormone (LH), follicle-stimulating hormone (FSH), human chorionic gonadotropin (HCG), thymosin, motilin, vasopressin, vasopressin derivatives [desmopressin, see Folia Endocrinologica Japonica, Vol. 54, No. 5, pp. 676–691 (1978)], oxytocin, calcitonin, parathyroid hormone (PTH), glucagon, secretin, pancreozymin, cholecystokinin, angiotensin, human placental lactogen, glucagon-like peptide (GLP-1) and derivatives thereof (see JP 6-80584 A, JP 7-2695 A, EP 658568, JP 8-245696 A, JP 8-269097 A, WO97/15296, WO97/31943, WO98/19698, WO98/43658, JP 10-511365 A, WO99/55310, JP 11-513983 A, CA2270320, WO99/64061, JP 11-514972 A, JP 2000-500505 A, WO2000/66138, WO2000/66142, WO2000/78333, JP 2001-11095, Tissue Eng. 7(1)35–44(2001), Diabetologia 43(10)1319–1328(2000), WO2000/34331, WO2000/34332, U.S. Pat. No. 6,268,343, U.S. 2001011071 A, U.S. 2001006943 A, EP 0733644, WO2000/77039, WO99/43707, WO99/43341, WO99/43706, WO99/43708, WO99/43705, WO99/29336, WO2000/37098, EP 0969016, U.S. Pat. No. 5,981,488, U.S. Pat. No. 5,958,909, WO93/25579, WO98/43658, EP 0869135, U.S. Pat. Nos. 5,614,492, 5,545,618, 5,120,712, 5,118,666, WO95/05848, WO91/11457, EP 0708179, WO96/06628, EP0658568, WO87/06941), glucose-dependent insulin secretory peptide (GIP), exendin and derivatives thereof (see WO2000/66629, WO2000/41546, WO99/07404, WO2000/09666, and U.S. Pat. No. 5,424,286), metastin and derivatives thereof (see WO2000/24890), and the like. Preferably, the peptide hormone is insulin and growth hormone, etc.

Growth hormone (hereinafter referred to as GH) originating from any animal species can be used, and is preferably human growth hormone (hereinafter referred to as hGH). Further, although natural products extracted from the pituitary gland can be used in the present invention, genetic recombinant type GH (see JP 6-12996 B and JP 6-48987 B) is preferred. The recombinant type hGH having the same structure as a natural type which does not have methionine at the N-terminal group is more preferred. Such GH may be in the form of a metal salt, and one being substantially free from a metal is also used. About 20K dalton type of hGH (see JP 7-101877 A and JP 10-265404 A) as well as about 22K dalton type of hGH can be used. Furthermore, the derivatives or related substances of hGH (see WO99/03887) can be used.

As the cytokines, for example, lymphokines, monokines, and the like can be used. As the lymphokines, there can be used, for example, interferons (alpha type, beta type, gamma type and the like), interleukins (IL-2, 3, 4, 5, 6, 7, 8, 9, 10, 11, 12 and the like) and the like. As the monokines include, for example, interleukin-1 (IL-1), tumor necrosis factor (TNF), and the like can be used. The cytokines are preferably lymphokines, and the like, more preferably interferons, and the like, especially preferably interferon-alpha.

As the peptide neurotransmitters, substance P, serotonin, GABA, and the like can be used.

As the hematopoietic factors, there can be used, for example, erythropoietin (EPO), colony stimulating factors (G-CSF, GM-CSF, M-CSF and the like), thrombopoietin (TPO), platelet growth stimulating factor, megakaryocyte potentiator, and the like.

As various growth factors, there can be used, for example, basic and acidic fibroblast growth factors (FGF) and their family (e.g., EGF, TGF-α, TGF-β, PDGF, acidic FGF, basic FGF, FGF-9, and the like), nerve growth factors (NGF) and their family (e.g., BDNF, NT-3, NT-4, CNTF, GDNF, and the like), insulin-like growth factors (e.g. IGF-1, IGF-2, and the like), bone morphogenetic protein (BMP) and their family, and the like.

As the enzymes include, there can be used, for example, superoxide dismutase (SOD), urokinase, tissue plasminogen activator (TPA), asparaginase, kallikrein, and the like.

As the polypeptide antibiotics, for example, polymixin B, colistin, gramicidin, bacitracin, and the like can be used.

As the analgesic peptides, for example, enkephalin, enkephalin derivatives (see U.S. Pat. No. 4,277,394 and EP 031567 A), endorphin, kyotorphin, and the like can be used.

As the vaccines, there can be used, for example, influenza vaccine, Japanese encephalitis vaccine, antirabies vaccine, hepatitis B vaccine, hepatitis A vaccine, cholera vaccine, DPT mixed vaccine, pneumococcus vaccine, diphteria vaccine, tetanus vaccine, polio vaccine, prostatic specific antigen vaccine, and the like.

Furthermore, the bioactive peptides include thymopoietin, dynorphin, bombesin, caerulein, thymostimulin, thymic humoral factor (THF), blood thymic factor (FTS) and derivatives thereof (see U.S. Pat. No. 4,229,438), other thymic factors [Igaku no Ayumi, Vol.125, No. 10, pp. 835–843 (1983)], neurotensin, bradykinin, endothelin-antagonistic peptides (see EP 436189 A, EP 457195 A and EP 496452 A, JP 3-94692 A and JP 3-130299 A), and the like.

In the present invention, when the bioactive peptide contains a metal, the metal contained in the bioactive peptide may be removed previously, if necessary, and, as a method for removing the metal, a known method can be used. For example, an insulin in the form of amorphous and containing a minimum amount of metal can be obtained by dialyzing an aqueous solution of insulin acidified with hydrochloric acid to water or a solution of ammonium acetate, followed by lyophilization.

As the non-peptidic bioactive substance of the present invention, for example, there may be mentioned one or more components selected from nourishing and health-promoting agents, antipyretic-analgesic-antiinflammatory agents, antipsychotic drugs, antianxiety drugs, antidepressants, hypnotic-sedatives, spasmolytics, central nervous system affecting drugs, cerebral metabolism ameliorators, antiepileptics, sympathomimetic agents, gastrointestinal function conditioning agents, antacids, antiulcer agents, antitussive-expectorants, antiemetics, respiratory stimulants, bronchodilators, antiallergic agents, dental buccal drugs, antihistamines, cardiotonics, antiarrhythmic agents, diuretics, hypotensive agents, vasoconstrictors, coronary vasodilators, peripheral vasodilators, antihyperlipidemic agents, cholagogues, antibiotics, chemotherapeutic agents, antidiabetic agents, drugs for osteoporosis, skeletal muscle relaxants, antimotion sickness drugs, hormones, alkaloid narcotics, sulfa drugs, drugs for treatment of gout, anticoagulants, anti-malignant tumor agents, agents for Alzheimer's disease and the like.

Examples of the nourishing and health-promoting agents include vitamins such as vitamin A, vitamin D, vitamin E (d-α-tocopherol acetate and the like), vitamin $B_1$ (dibenzoylthiamine, fursultiamine hydrochloride and the like), vitamin $B_2$ (riboflavin butyrate and the like), vitamin $B_6$ (pyridoxine hydrochloride and the like), vitamin C (ascorbic acid, sodium L-ascorbate and the like), vitamin $B_{12}$ (hydroxocobalamin acetate and the like) and the like; minerals such as calcium, magnesium and iron; amino acids; oligosaccharides; galenical; and the like. Examples of the antipyretic-analgesic-antiinflammatory agents include aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, tolfenamic acid, mefenamic acid, diclofenac sodium, flufenamic acid, salicylamide, aminopyrine, ketoprofen, indomethacin, bucolome, pentazocine and the like. Examples of the antipsychotic drugs include chlorpromazine, reserpine and the like. Examples of the antianxiety drugs include alprazolam, chlordiazepoxide, diazepam and the like. Examples of the antidepressants include imipramine, maprotiline, amphetamine and the like.

Examples of the hypnotic-sedatives include estazolam, nitrazepam, diazepam, perlapine, phenobarbital sodium and the like. Examples of the spasmolytics include scopolamine hydrobromide, diphenhydramine hydrochloride, papaverine hydrochloride and the like. Examples of the central nervous system affecting drugs include citicoline, rotirenine and the like. Examples of the cerebral metabolism ameliorators include vinpocetine, meclofenoxate hydrochloride and the like. Examples of the antiepileptics include phenytoin, carbamazepine and the like. Examples of the sympathomimetic agents include isoproterenol hydrochloride and the like. Examples of the gastrointestinal function conditioning agents include stomachic-digestives such as gentian, swertia herb, nux vomica, phellodendron bark, bitter orange peel, Condurango, cinnamon oil and the like; intestinal function controlling drugs such as perperine hydrochloride, resistant lactic acid bacterium, *Lactobacillus bifidus* and the like. Examples of the antacids include magnesium carbonate, sodium hydrogen carbonate, magnesium aluminometasilicate, synthetic hydrotalcite, precipitated calcium carbonate, magnesium oxide and the like. Examples of the antiulcer agents include lansoprazole, omeprazole, rabeprazole, pantoprazole, famotidine, cimetidine, ranitidine hydrochloride and the like.

Examples of the antitussive-expectorants include chloperastine hydrochloride, dextromethorphan hydrobromide, theophylline, potassium guaiacolsulfonate, guaifenesin, codeine phosphate and the like. Examples of the antiemetics include diphenidol hydrochloride, metoclopramide and the like. Examples of the respiratory stimulants include levallorphan tatrate and the like. Examples of the bronchodilators include theophylline, salbutamol sulfate and the like. Examples of the antiallergic agents include amlexanox, seratrodast and the like. Examples of the dental buccal drugs include oxytetracycline, triamcinolone acetonide, chlorhexidine hydrochloride, lidocaine and the like. Examples of the antihistamines include diphenhydramine hydrochloride, promethazine, isothipendyl hydrochloride, dl-chlorpheniramine maleate and the like. Examples of the cardiotonics include caffeine, digoxin and the like. Examples of the antiarryhythmic agents include procainamide hydrochloride, propranolol hydrochloride, pindolol and the like. Examples of the diuretics include isosorbide, furosemide and the like. Examples of the hypotensive agents include delapril hydrochloride, captopril, hexamethonium bromide, hydralazine hydrochloride, labetalol hydrochloride, manidipine hydrochloride, losartan, eprosartan, candesartan cilexetil (TCV-116), candesartan (CV-11974), valsartan, telmisartan, irbesartan, tasosartan, ormesartan and the like. As the hypotensive agents, candesartan, candesartan cilexetil and the like are preferred, and candesartan and the like are specifically preferred.

Examples of the vasoconstrictors include phenylephrine hydrochloride and the like. Examples of the coronary vasodilators include carbocromen hydrochloride, molsidomine, verapamil hydrochloride and the like. Examples of the peripheral vasodilators include cinnarizine and the like. Examples of the antihyperlipidemic agents include cerivastatin sodium, simvastatin, pravastatin sodium and the like. Examples of the cholagogues include dehydrocholic acid, trepibutone and the like. Examples of the antibiotics include cephem antibiotics such as cefalexin, amoxicillin, pivmecillinam hydrochloride, cefotiam dihydrochloride, cefozopran hydrochloride, cefinenoxime hydrochloride, cefsluodin sodium, etc.; synthetic antibacterials such as ampicillin, cyclacillin, sulbenicillin sodium, nalidixic acid, enoxacin, etc.; monobactam antibiotics such as carumonam sodium; penem antibiotics, carbapenem antibiotics, etc.; and the like. Examples of the chemotherapeutic agents include sulfamethizole hydrochloride, thiazosulfone and the like. Examples of the antidiabetic agents include tolbutamide, voglibose, pioglitazone (hydrochloride), troglitazone, 5-[[4-[2-(methyl-2-pyridinylamino)ethoxy]phenyl]methyl]-2,4-thiazolidinedione (BRL-49653), acarbose, miglitol, emiglitate and the like. Examples of the drugs for osteoporosis include ipriflavone and the like. Examples of the skeletal muscle relaxants include methocarbamol and the like. Examples of the antimotion sickness drugs include meclizine hydrochloride, dimenhydrinate and the like.

Examples of the hormones include riothyroinine sodium, dexamethasone sodium phosphate, prednisolone, oxendolone, leupororelin acetate and the like. Examples of the alkaloid narcotics include opium, morphine hydrochloride, ipecac, oxycodone hydrochloride, opium alkaloids hydrochlorides, cocaine hydrochloride and the like. Examples of the sulfa drugs include sulfanilamide, sufamethizole and the like. Examples of the drugs for treatment of gout include allopurinol, colchicine and the like. Examples of the anti-coagulants include dicoumarol and the like. Examples of the anti-malignant tumor agents include 5-fluorouracil, uracil, mitomycin and the like. Examples of the agents for Alzheimer's disease include idebenone, vinpocetine and the like.

As the non-peptidic bioactive substance in the present invention, a compound having an oxygen atom in the molecule, specifically, a compound having an ether bond or a carbonyl group is preferred. Such compound includes a compound represented by the formula (I):

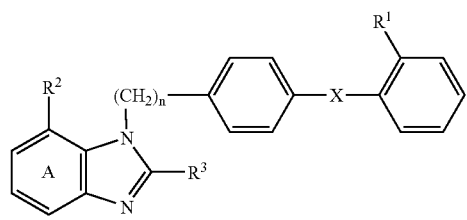

or a salt thereof.

In the above-mentioned formula (I), examples of the group capable of forming an anion (a group having hydrogen atom that may be liberated as a proton) as $R^1$ include (1) a carboxyl group, (2) a tetrazolyl group, (3) a trifluoromethanesulfonic acid amide group (—$NHSO_2CF_3$), (4) a phosphoric acid group, (5) a sulfonic acid group, (6) an optionally substituted 5- to 7-membered (preferably 5- or 6-membered) monocyclic heterocycle residue containing one or two or more of N, S and O, and the like.

Examples of the above-mentioned "optionally substituted 5- to 7-membered (preferably 5- or 6-membered) monocyclic heterocycle residue containing one or two or more of N, S and O" include

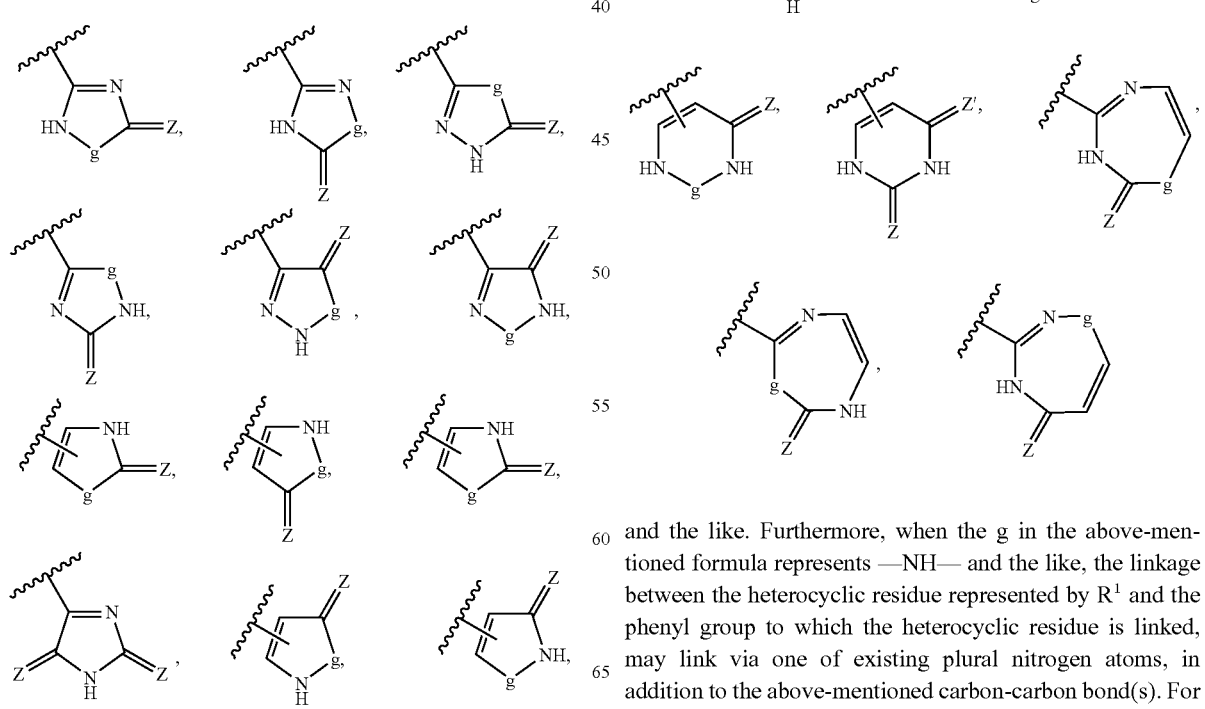

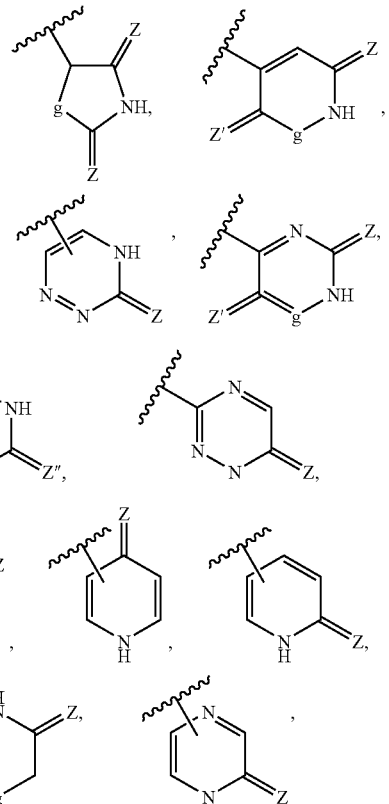

and the like. Furthermore, when the g in the above-mentioned formula represents —NH— and the like, the linkage between the heterocyclic residue represented by $R^1$ and the phenyl group to which the heterocyclic residue is linked, may link via one of existing plural nitrogen atoms, in addition to the above-mentioned carbon-carbon bond(s). For example, when $R^1$ is represented by the formula:

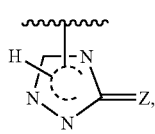

specifically, examples thereof are

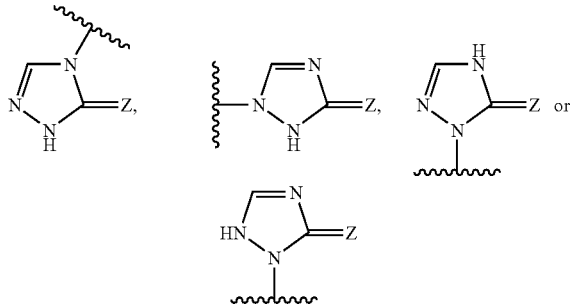

and the like, respectively. The other examples of the link via a nitrogen atom include

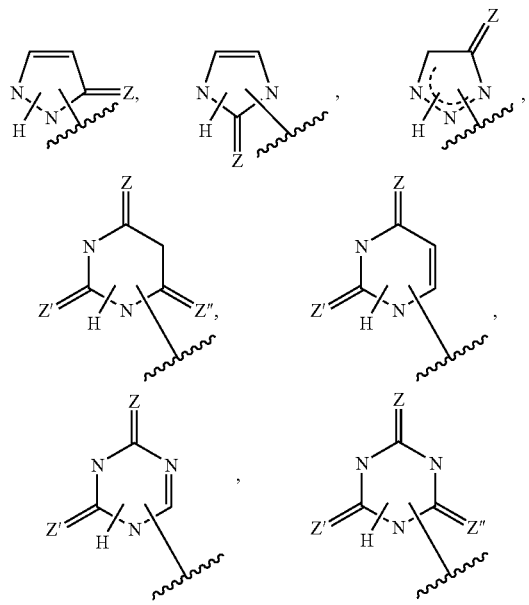

and the like.

In the above-mentioned formula, g represents —$CH_2$—, —NH—, —O— or —$S(O)_m$—, >=Z, >=Z' and >=Z'' each represents a carbonyl group, a thiocarbonyl group or an optionally oxidized sulfur atom (e.g., S, S(O), $S(O)_2$ and the like) (preferably a carbonyl or a thiocarbonyl group, more preferably a carbonyl group), respectively, and m represents 0, 1 or 2.

The heterocyclic residue represented by $R^1$ is preferably groups obtained by eliminating one hydrogen atom from a ring that has both —NH— or —OH group as a proton donor, and a carbonyl group, a thiocarbonyl group, a sulfinyl group, or the like as a proton acceptor, simultaneously, such as an oxadiazolone ring, an oxadiathiazolone ring, a thiadiazolone group, or the like. Furthermore, the heterocyclic residue represented by $R^1$ may form a condensed ring group by linking substituents on the ring. As the heterocyclic residue represented by $R^1$, a 5- or 6-membered ring residue is preferred, and a 5-membered residue is more preferred.

As the heterocyclic residue represented by $R^1$, a group represented by the formula:

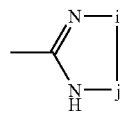

wherein i represents —O— or —S—, j represents >=O, >=S or >=$S(O)_m$, m is as defined above (among these, 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl, especially 2,5-dihydro-5-oxo-1,2,4-oxadiazol-3-yl) and the like are preferred.

Furthermore, the above-mentioned heterocyclic residue ($R^1$) has tautomers as shown below. For example, when Z=O and g=O in the following formula:

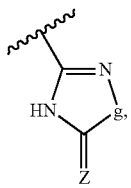

three tautomers a', b' and c', such as

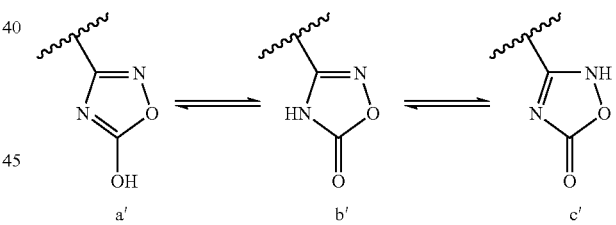

are present, and the heterocyclic residue represented by the formula:

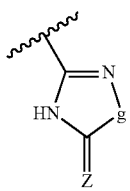

encompasses all of the above-mentioned a', b' and c'.

The group capable of forming an anion as $R^1$ may be protected with an optionally substituted lower ($C_{1-4}$) alkyl group or an acyl group (e.g., a lower ($C_{2-5}$) alkanoyl, a benzoyl, etc.), and the like, at substitutable position(s).

The optionally substituted lower ($C_{1-4}$) alkyl group include, for example, (1) a lower ($C_{1-4}$) alkyl group optionally substituted with 1 to 3 phenyl group(s) optionally having a halogen atom, nitro, lower ($C_{1-4}$) alkyl, lower ($C_{1-4}$) alkoxy and the like (e.g., methyl, triphenylmethyl, p-methoxybenzyl, p-nitrobenzyl and the like), (2) a lower ($C_{1-4}$) alkoxy-lower ($C_{1-4}$) alkyl group (e.g., methoxymethyl, ethoxymethyl and the like), (3) the formula —CH($R^4$)—OCOR$^5$ [wherein $R^4$ represents (a) hydrogen, (b) a straight chain or branched lower alkyl group having 1–6 carbon atom(s) (e.g., methyl, ethyl, n-propyl, isopropyl, n-butyl, isobutyl, t-butyl, n-pentyl, isopentyl, neopentyl and the like), (c) a straight chain or branched lower alkenyl group having 2–6 carbon atoms or (d) a cycloalkyl group having 3–8 carbon atoms (e.g., cyclopentyl, cyclohexyl, cycloheptyl and the like), $R^5$ represents (a) a straight chain or branched lower alkyl group having 1–6 carbon atom(s) (e.g., methyl, ethyl, n-propyl, isopropyl, n-butyl, isobutyl, sec-butyl, t-butyl, n-pentyl, isopentyl, neopentyl and the like), (b) a straight chain or branched lower alkenyl group having 2–6 carbon atoms, (c) a lower alkyl group having 1 to 3 carbon atom(s) substituted with a cycloalkyl group having 3–8 carbon atoms (e.g., cyclopentyl, cyclohexyl, cycloheptyl and the like) or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., benzyl, p-chlorobenzyl, phenethyl, cyclopentylmethyl, cyclohexylmethyl and the like), (d) a lower alkenyl group having 2 to 3 carbon atoms substituted by a cycloalkyl having 3–8 carbon atoms or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., a group having alkenyl portion(s) such as vinyl, propenyl, allyl, isopropenyl and the like, such as cinnamyl, and the like), (e) an optionally substituted aryl group (e.g., a phenyl or a naphthyl group and the like, each of which may have a halogen atom, nitro, lower ($C_{1-4}$) alkyl, lower ($C_{1-4}$) alkoxy and the like, such as phenyl, p-tolyl, naphthyl and the like), (f) a straight or a branched lower alkoxy group having 1–6 carbon atom(s) (e.g., methoxy, ethoxy, n-propoxy, isopropoxy, n-butoxy, isobutoxy, sec-butoxy, t-butoxy, n-pentyloxy, isopentyloxy, neopentyloxy and the like), (g) a straight chain or branched lower alkenyloxy group having 2 to 8 carbon atoms (e.g., allyloxy, isobutenyloxy and the like), (h) a cycloalkyloxy group having 3–8 carbon atoms (e.g., cyclopentyloxy, cyclohexyloxy, cycloheptyloxy and the like), (i) a lower alkoxy group having 1 to 3 carbon atom(s) substituted with a cycloalkyl having 3–8 carbon atoms (e.g., cyclopentyl, cyclohexyl, cycloheptyl and the like) or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., a group having alkoxy portion(s) such as methoxy, ethoxy, n-propoxy, isopropoxy and the like, such as benzyloxy, phenethyloxy, cyclopentylmethoxy, cyclohexylmethoxy and the like), (j) a lower alkenyloxy group having 2 to 3 carbon atoms substituted with a cycloalkyl having 3–8 carbon atoms (e.g., cyclopentyl, cyclohexyl, cycloheptyl and the like) or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., a group having alkenyloxy portion(s) such as vinyloxy, propenyloxy, allyloxy, isopropenyloxy and the like, such as cinnamyloxy and the like, and the like), (k) an optionally substituted aryloxy group (e.g., phenoxy or naphthoxy group and the like, each of which may have a halogen atom, nitro, lower ($C_{1-4}$) alkyl, lower ($C_{1-4}$) alkoxy and the like, such as phenoxy, p-nitrophenoxy, naphthoxy and the like, and the like)], and the like.

Furthermore, the group capable of forming an anion as $R^1$ may have substituent(s) such as an optionally substituted lower ($C_{1-4}$) alkyl group (which includes the groups similar to the "optionally substituted lower ($C_{1-4}$) alkyl group" that is exemplified as protective groups for the group capable of forming an anion as the above-mentioned $R^1$), a halogen atom, nitro, cyano, lower ($C_{1-4}$) alkoxy, an amino optionally substituted with 1 or 2 of lower ($C_{1-4}$) alkyl(s) and the like, at the substitutable position(s), in addition to the protective groups such as the above-mentioned optionally substituted lower ($C_{1-4}$) alkyl group or acyl group (e.g., a lower ($C_{2-5}$) alkanoyl, a benzoyl and the like).

In the above-mentioned formula, the group which may be converted into the group capable of forming an anion as $R^1$ (a group having hydrogen atom that may be liberated as a proton) may be a group which can be converted into the group capable of forming an anion by a reaction under biological, i.e., physiological conditions (for example, an in vivo reaction such as oxidation, reduction, hydrolysis or the like with an in vivo enzyme, and the like) (so-called prodrug), or may be a group which can be converted into a group capable of forming an anion represented by $R^1$ by a chemical reaction, such as cyano, an N-hydroxycarbamimidoyl group (—C(=N—OH)—NH$_2$), or (1) a carboxyl group, (2) a tetrazolyl group, (3) a trifluoromethanesulfonic acid amide group (—NHSO$_2$CF$_3$), (4) a phosphoric acid group, (5) a sulfonic acid group, and (6) an optionally substituted 5- to 7-membered (preferably 5-or 6-membered) monocyclic heterocycle residue containing one or two or more of N, S and O, each of which has been protected with an optionally substituted lower ($C_{1-4}$) alkyl group or an acyl group (so-called synthetic intermediate).

Preferred examples of $R^1$ include a carboxyl, a tetrazolyl, or a 2,5-dihydro-5-oxo-1,2,4-oxadiazol-3-yl (preferably tetrazolyl) optionally protected with an optionally substituted lower ($C_{1-4}$) alkyl (e.g., methyl, triphenylmethyl, methoxymethyl, ethoxymethyl, p-methoxybenzyl, p-nitrobenzyl and the like) or an acyl group (e.g., lower ($C_{2-5}$) alkanoyl, benzoyl and the like), or a cyano, an N-hydroxycarbamimidoyl (preferably cyano), and specifically, cyano is preferably used.

In the above-mentioned formula, X represents that the adjacent phenylene group and phenyl group are linked directly or via a spacer of an atomic chain having two or less atom(s) (preferably linked directly), and the spacer of an atomic chain having two or less atom(s) may be any divalent chain whose straight chain portion is constituted of 1 or 2 atom(s). The chain may also have side chain(s). Specifically, it includes a lower ($C_{1-4}$) alkylene whose straight chain portion is constituted of 1 or 2 atoms, —CO—, —O—, —S—, —NH—, —CO—NH—, —O—CH$_2$—, —S—CH$_2$—, —CH=CH— and the like.

In the above-mentioned formula, n represents an integer of 1 or 2 (preferably 1).

In the above-mentioned formula, ring A represents a benzene ring which may be further substituted in addition to the substituent $R^2$, and examples of the substituent include (1) halogen (e.g., F, Cl, Br and the like), (2) cyano, (3) nitro, (4) optionally substituted lower ($C_{1-4}$) alkyl, (5) lower ($C_{1-4}$) alkoxy, (6) an optionally substituted amino group (e.g., amino, N-lower ($C_{1-4}$) alkylamino (e.g., methylamino and the like), N,N-dilower ($C_{1-4}$) alkylamino (e.g., dimethylamino and the like), N-arylamino (e.g., phenylamino and the like), alicyclic amino (e.g., morpholino, piperidino, piperadino, N-phenylpiperadino and the like), and the like), (7) a group represented by the formula —CO-D' [wherein D' represents a hydroxy group or lower ($C_{1-4}$) alkoxy in which the alkyl portion may be substituted with a hydroxy group, lower ($C_{1-4}$) alkoxy, lower ($C_{2-6}$) alkanoyloxy (e.g., acetoxy, pivaloyloxy and the like), lower ($C_{1-6}$) alkoxycarbonyloxy (e.g., methoxycarbonyloxy, ethoxycarbonyloxy and the like) or lower ($C_{3-6}$) cycloalkoxycarbonyloxy (e.g., cyclohexyloxycarbonyloxy and the like)], (8) tetrazolyl, a trifluoromethanesulfonic acid amide group, a phosphoric acid group or a sulfonic acid group, each of which is optionally protected with optionally substituted lower ($C_{1-4}$) alkyl (including the groups similar to the "optionally substituted lower ($C_{1-4}$) alkyl group" exemplified as protective groups for the group capable of forming an anion as the abovementioned $R^1$) or acyl (e.g., lower ($C_{2-5}$) alkanoyl, benzoyl and the like), or the like.

One or two of these substituents may be present at the substitutable position(s) of the benzene ring, simultaneously, while preferred substituent which is further possessed by ring A in addition to the substituent $R^2$ is optionally substituted lower ($C_{1-4}$) alkyl (e.g., lower ($C_{1-4}$) alkyl optionally substituted with a hydroxy group, a carboxyl group, halogen, etc., and the like), halogen, and the like, and more preferably, the ring A does not have any substituent except for the substituent $R^2$.

In the above-mentioned formula, examples of the group capable of forming an anion as $R^2$ (a group having hydrogen atom that may be liberated as a proton) include (1) a carboxyl group which may be esterified or amidated, (2) a tetrazolyl group, (3) a trifluoromethanesulfonic acid amide group (—$NHSO_2CF_3$), (4) a phosphoric acid group, (5) a sulfonic acid group, and the like. These groups may be protected with an optionally substituted lower alkyl group (including a group similar to the "optionally substituted lower ($C_{1-4}$) alkyl group" exemplified as protective groups for the group capable of forming an anion as the abovementioned $R^1$) or an acyl group (e.g., lower ($C_{2-5}$) alkanoyl, benzoyl, and the like), and may be any group as long as it is a group capable of forming an anion or a group which may be converted into such a group under biological, i.e., physiological conditions (for example, an in vivo reaction such as oxidation, reduction or hydrolysis, and the like with an in vivo enzyme, and the like), or chemically.

Examples of the carboxyl which may be esterified or amidated, as $R^2$, include a group represented by the formula —CO-D [wherein D represents (1) a hydroxy group, (2) optionally substituted amino (for example, amino, N-lower ($C_{1-4}$) alkylamino, N,N-dilower ($C_{1-4}$) alkylamino and the like), (3) optionally substituted alkoxy {e.g., (i) a lower ($C_{1-6}$) alkoxy group in which the alkyl portion is optionally substituted with a hydroxy group, optionally substituted amino (e.g., amino, N-lower ($C_{1-4}$) alkylamino, N,N-dilower ($C_{1-4}$) alkylamino, piperidino, morpholino and the like), halogen, lower ($C_{1-6}$) alkoxy, lower ($C_{1-6}$) alkylthio, lower ($C_{3-8}$) cycloalkoxy or optionally substituted dioxolenyl (e.g., 5-methyl-2-oxo-1,3-dioxolen-4-yl and the like), or (ii) a group of the formula —O—CH($R^6$)—OCOR$^7$ [wherein $R^6$ represents (a) hydrogen, (b) a straight chain or branched lower alkyl group having 1–6 carbon atom(s) (e.g., methyl, ethyl, n-propyl, isopropyl, n-butyl, isobutyl, t-butyl, n-pentyl, isopentyl, neopentyl and the like), (c) a straight chain or branched lower alkenyl group having 2–6 carbon atoms or (d) a cycloalkyl group having 3–8 carbon atoms (e.g., cyclopentyl, cyclohexyl, cycloheptyl and the like), $R^7$ represents (a) a straight chain or branched lower alkyl group having 1–6 carbon atom(s) (e.g., methyl, ethyl, n-propyl, isopropyl, n-butyl, isobutyl, sec-butyl, t-butyl, n-pentyl, isopentyl, neopentyl and the like), (b) a straight chain or branched lower alkenyl group having 2–6 carbon atoms, (c) a lower alkyl group having 1 to 3 carbon atom(s) substituted with a cycloalkyl group having 3–8 carbon atoms (e.g., cyclopentyl, cyclohexyl, cycloheptyl and the like) or an optionally substituted aryl group (e.g., a phenyl or a naphthyl group and the like, each of which may have a halogen atom, nitro, lower ($C_{1-4}$) alkyl, lower ($C_{1-4}$) alkoxy and the like) (e.g., benzyl, p-chlorobenzyl, phenethyl, cyclopentylmethyl, cyclohexylmethyl and the like), (d) a lower alkenyl group having 2 to 3 carbon atoms substituted with a cycloalkyl having 3–8 carbon atoms or an optionally substituted aryl group (e.g., phenyl or naphthyl group and the like, each of which may have a halogen atom, nitro, lower ($C_{1-4}$) alkyl, lower ($C_{1-4}$) alkoxy and the like) (e.g., a group having an alkenyl portion such as vinyl, propenyl, allyl, isopropenyl, and the like, for example, cinnamyl, and the like), (e) an optionally substituted aryl group (e.g., a phenyl or naphthyl group and the like, each of which may have a halogen atom, nitro, lower ($C_{1-4}$) alkyl, lower ($C_{1-4}$) alkoxy and the like, such as phenyl, p-tolyl, naphthyl and the like), (f) a straight chain or branched lower alkoxy group having 1–6 carbon atom(s) (e.g., methoxy, ethoxy, n-propoxy, isopropoxy, n-butoxy, isobutoxy, sec-butoxy, t-butoxy, n-pentyloxy, isopentyloxy, neopentyloxy and the like), (g) a straight chain or branched lower alkenyloxy group having 2 to 8 carbon atoms (e.g., allyloxy, isobutenyloxy and the like), (h) a cycloalkyloxy group having 3–8 carbon atoms (e.g., cyclopentyloxy, cyclohexyloxy, cycloheptyloxy and the like), (i) a lower alkoxy group having 1 to 3 carbon atom(s) substituted with a cycloalkyl having 3–8 carbon atoms (e.g., cyclopentyl, cyclohexyl, cycloheptyl and the like) or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., a group having alkoxy portion(s) such as methoxy, ethoxy, n-propoxy, isopropoxy and the like, such as benzyloxy, phenethyloxy, cyclopentylmethoxy, cyclohexylmethoxy and the like), (j) a lower alkenyloxy group having 2 to 3 carbon atoms substituted with a cycloalkyl having 3–8 carbon atoms (e.g., cyclopentyl, cyclohexyl, cycloheptyl and the like) or an optionally substituted aryl group (e.g., a phenyl or naphthyl group and the like, each of which may have a halogen atom, nitro, lower ($C_{1-4}$) alkyl, lower ($C_{1-4}$) alkoxy and the like) (e.g., a group having alkenyloxy portion(s) such as vinyloxy, propenyloxy, allyloxy, isopropenyloxy and the like, such as cinnamyloxy and the like) or (k) an optionally substituted aryloxy group (e.g., phenoxy or naphthoxy group and the like, each of which may have a halogen atom, nitro, lower ($C_{1-4}$) alkyl, lower ($C_{1-4}$) alkoxy and the like, such as phenoxy, p-nitro phenoxy, naphthoxy and the like)]}, and the like], and the like.

As $R^2$, an optionally esterified carboxyl is preferred, and the specific examples thereof include —COOH and a salt thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl and the like, and may be any group as long as it is a group capable of forming an anion (e.g., COO⁻, its derivative, and the like) or a group which may be converted into such a group under biological, i.e., physiological conditions (for example, an in vivo reaction such as oxidation, reduction or hydrolysis, and the like with an in vivo enzyme, and the like), or chemically, or it may be carboxyl group or a prodrug thereof.

The above-mentioned $R^2$ is preferably the group represented by the formula —CO-D [wherein D represents (1) a hydroxy group or (2) lower ($C_{1-4}$) alkoxy in which the alkyl portion is optionally substituted with a hydroxy group, amino, halogen, lower ($C_{2-6}$) alkanoyloxy (e.g., acetoxy, pivaloyloxy and the like), lower ($C_{3-8}$) cycloalkanoyloxy, lower ($C_{1-6}$) alkoxycarbonyloxy (e.g., methoxycarbonyloxy, ethoxycarbonyloxy and the like), lower ($C_{3-8}$) cycloalkoxycarbonyloxy (e.g., cyclohexyloxycarbonyloxy and the like), lower ($C_{1-4}$) alkoxy or lower ($C_{3-8}$) cycloalkoxy]. Among these, carboxyl esterified with a lower ($C_{1-4}$) alkyl (preferably methyl or ethyl) is preferred.

In the above-mentioned formula, examples of the "hydrocarbon residue" of the "hydrocarbon residue which may link via a heteroatom and may be substituted" represented by $R^3$ include (1) an alkyl group, (2) an alkenyl group, (3) an alkynyl group, (4) a cycloalkyl group, (5) an aryl group, (6) an aralkyl group and the like. Among these, an alkyl group, an alkenyl group and a cycloalkyl group are preferred.

The alkyl group of the above-mentioned (1) may be any of straight chain or branched lower alkyl groups having about 1 to 8 carbon atom(s) such as methyl, ethyl, propyl, isopropyl, butyl, isobutyl, sec-butyl, t-butyl, pentyl, i-pentyl, hexyl, heptyl, octyl and the like.

The alkenyl group of the above-mentioned (2) may be any of straight chain or branched lower alkenyl groups having 2 to 8 carbon atoms such as vinyl, propenyl, 2-butenyl, 3-butenyl, isobutenyl, 2-octenyl and the like.

The alkynyl group of the above-mentioned (3) may be any of straight chain or branched lower alkynyl groups having 2 to 8 carbon atoms such as ethynyl, 2-propynyl, 2-butynyl, 2-pentynyl, 2-octynyl and the like.

The cycloalkyl group of the above-mentioned (4) include lower cycloalkyl having about 3 to 6 carbon atoms such as cyclopropyl, cyclobutyl, cyclopentyl, cyclohexyl and the like.

Each of the above-mentioned alkyl group, alkenyl group, alkynyl group or cycloalkyl group may be substituted with a hydroxy group, an optionally substituted amino group (e.g., amino, N-lower ($C_{1-4}$) alkylamino, N,N-dilower ($C_{1-4}$) alkylamino and the like), halogen, a lower ($C_{1-4}$) alkoxy group, a lower ($C_{1-4}$) alkylthio group and the like.

The aryl group of the above-mentioned (5) includes, for example, phenyl and the like, and the aralkyl group of the above-mentioned (6) include a phenyl-lower ($C_{1-4}$) alkyl and the like such as benzyl, phenethyl and the like.

Each of the above-mentioned aralkyl group or aryl group may have, at the substitutable position(s) on the benzene ring, for example, halogen (e.g., F, Cl, Br and the like), nitro, an optionally substituted amino group (e.g., amino, N-lower ($C_{1-4}$) alkylamino, N,N-dilower ($C_{1-4}$) alkylamino and the like), lower ($C_{1-4}$) alkoxy (e.g., methoxy, ethoxy and the like), lower ($C_{1-4}$) alkylthio (e.g., methylthio, ethylthio and the like), lower ($C_{1-4}$) alkyl (e.g., methyl, ethyl and the like) and the like.

Among the above-mentioned groups, as the "hydrocarbon residue" of the "hydrocarbon residue which may link via a heteroatom and may be substituted" represented by $R^3$, an optionally substituted alkyl or alkenyl group (e.g., lower ($C_{1-5}$) alkyl or lower ($C_{2-5}$) alkenyl group and the like, each of which is optionally substituted with a hydroxy group, an amino group, halogen or a lower ($C_{1-4}$) alkoxy group) are preferred. Among these, a lower ($C_{1-5}$) alkyl (more preferably ethyl) is preferred.

The "heteroatom" of the "hydrocarbon residue which may link via a heteroatom and may be substituted" represented by $R^3$ include —O—, —S(O)$_m$— [m represents an integer of 0 to 2], —NR'— [R' represents a hydrogen atom or lower ($C_{1-4}$) alkyl] and the like. Among these, —O— is preferably used.

Among the above-mentioned groups, as $R^3$, a lower ($C_{1-4}$) alkyl or lower ($C_{2-5}$) alkenyl group and the like, each of which may be linked via —O—, —S(O)$_m$— [m represents an integer of 0 to 2] or —NR'— [R' represents a hydrogen atom or lower ($C_{1-4}$) alkyl] and may be substituted with a substituent selected from a hydroxy group, an amino group, halogen and lower ($C_{1-4}$) alkoxy group, is preferred. Among these, a lower ($C_{1-5}$) alkyl or a lower ($C_{1-5}$) alkoxy (more preferably ethoxy) is preferred.

Among the compounds represented by the formula (I), a benzimidazol-7-carboxylic acid derivative represented by the formula (I'):

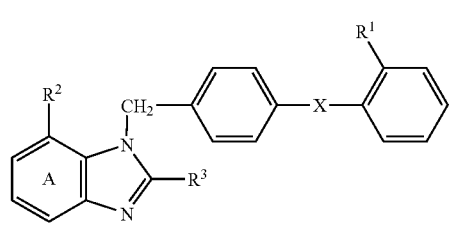

wherein $R^1$ is (1) a carboxyl group, (2) a tetrazolyl group or (3) a group represented by the formula:

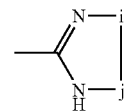

wherein i represents —O— or —S—, j represents >=O, >=S or >=S(O)$_m$, m is as defined above, ring A represents a benzene ring which may be further substituted with optionally substituted lower ($C_{1-4}$) alkyl (e.g., lower ($C_{1-4}$) alkyl optionally substituted with a hydroxy group, a carboxyl group, halogen and the like) or halogen and the like, in addition to the substituent $R^2$ (preferably a benzene ring that does not have any substituent except for $R^2$), $R^2$ represents a group represented by the formula —CO-D [wherein D represents (1) a hydroxy group or (2) lower ($C_{1-4}$) alkoxy wherein the alkyl portion is optionally substituted with a hydroxy group, amino, halogen, lower ($C_{2-6}$) alkanoyloxy (e.g., acetoxy, pivaloyloxy and the like), lower ($C_{3-8}$) cycloalkanoyloxy, lower ($C_{1-6}$) alkoxycarbonyloxy (e.g., methoxycarbonyloxy, ethoxycarbonyloxy and the like), lower ($C_{3-8}$) cycloalkoxycarbonyloxy (e.g., cyclohexyloxycarbonyloxy and the like), lower ($C_{1-4}$) alkoxy or a lower ($C_{3-8}$) cycloalkoxy], $R^3$ is a lower ($C_{1-5}$) alkyl or lower ($C_{2-5}$) alkenyl group which may link via —O—, —S(O)$_m$— [m represents an integer of 0 to 2] or —NR'— [R' represents a hydrogen atom or lower ($C_{1-4}$) alkyl] and may be substituted with a substituent selected from a hydroxy group, an amino group, halogen and a lower ($C_{1-4}$) alkoxy group (preferably lower ($C_{1-5}$) alkyl or lower ($C_{1-5}$) alkoxy; more preferably ethoxy), or a pharmacologically acceptable salt thereof, is preferred. Among these, preferred are 2-ethoxy-1-[[2'-(1H-tetrazol-5-yl) biphenyl-4-yl]methyl]benzimidazol-7-carboxylic acid [Candesartan], 1-(cyclohexyloxycarbonyloxy)ethyl 2-ethoxy-1-[[2'-(1H-tetrazol-5-yl)biphenyl-4-yl]methyl]benzimidazol-7-carboxylate [Candesartan cilexetil], pivaloyloxymethyl 2-ethoxy-1-[[2'-(1H-tetrazol-5-yl)biphenyl-4-yl]methyl]benzimidazol-7-carboxylate, 2-ethoxy-1-[[2'-(2,5-dihydro-5-oxo-1,2,4-oxadiazol-3-yl)biphenyl-4-yl]methyl]benzimidazol-7-carboxylic acid or a salt thereof and the like.

The above-mentioned benzimidazol derivatives can be synthesized by, for example, known methods disclosed in EP 425921, EP 459136, EP 553879, EP 578125, EP 520423, EP 668272 and the like, or a similar manner thereto, and the like. Further, when Candesartan cilexetil is used, it is preferable to use the stable C type crystal disclosed in EP 459136.

While the amount of the bioactive substance formulated into the sustained-release preparation of the present invention varies depending on the kind of the bioactive substance and the like, it is generally about 0.1 to 50% (W/W), preferably about 0.2 to 30% (W/W), and more preferably about 0.5 to 20% (W/W) in case of a bioactive peptide, or it is generally about 0.1 to 60% (W/W), preferably about 0.2 to 40% (W/W), and more preferably about 0.5 to 30% (W/W) in case of a non-peptidic bioactive substance.

The polymer used in the present invention is a polymer which is slightly soluble or insoluble in water and has biocompatibility. Examples thereof include polystyrene, poly-acrylic acid, poly-methacrylic acid, a copolymer of acrylic acid and methacrylic acid, nylon, tetlon, silicone polymer, dextran stearate, ethylcellulose, acetylcellulose, nitrocellulose, polyurethane, ethylene vinyl acetate copolymer, polyvinyl acetate, polyvinyl alcohol, polyacrylicamide and the like. Furthermore, examples of the biodegradable polymer include polymers synthesized from one or more of α-hydroxycarboxylic acids (e.g., glycolic acid, lactic acid and the like), hydroxydicarboxylic acids (e.g., malic acid and the like), hydroxytricarboxylic acids (e.g., citric acid and the like) etc., by catalyst-free dehydration polycondensation, which have free carboxyl group(s), or a mixture thereof, poly-α-cyanoacrylic esters, polyamino acids (e.g., poly-y-benzyl-L-glutamic acid and the like), maleic anhydride polymers (e.g., a styrene/maleic acid polymer and the like), and the like. The polymer may be a homopolymer or a copolymer. The type of polymerization may be of random, block or graft. When the above-mentioned α-hydroxycarboxylic acids, hydroxydicarboxylic acids and hydroxytricarboxylic acids have optically active centers in their molecular structures, they may be any of the D-, L- and DL-configurations.

Among these polymers, the biodegradable polymer having a free terminal carboxyl group such as a polymer synthesized from α-hydroxycarboxylic acids (e.g., glycolic acid, lactic acid and the like) (e.g., poly-lactic acid, lactic acid/glycolic acid copolymer, and the like), poly-α-cyanoacrylic acid esters and the like are preferred.

The biodegradable polymer is more preferably a polymer synthesized from α-hydroxycarboxylic acids and the like, especially preferably a lactic acid/glycolic acid polymer and the like.

Not only homopolymers such as poly-lactic acid, poly-glycolic acid, etc., but also lactic acid/glycolic acid copolymers are sometimes simply referred to as the lactic acid/glycolic acid polymer herein inclusively.

When the lactic acid/glycolic acid polymer (a lactic acid/glycolic acid copolymer or homopolymer) is used as the biodegradable polymer, its composition ratio (mol %) is preferably about 100/0 to about 40/60, more preferably about 85/15 to about 50/50.

The weight-average molecular weight of the above-described lactic acid/glycolic acid polymer is preferably about 3,000 to about 50,000, more preferably about 3,000 to about 25,000, further more preferably about 5,000 to about 20,000.

The degree of dispersion (weight-average molecular weight/number-average molecular weight) of the lactic acid/glycolic acid polymer is preferably about 1.2 to about 4.0, more preferably about 1.5 to about 3.5.

Regarding the weight-average molecular weight and the degree of dispersion used herein, the former is a value converted into polystyrene as determined by gel permeation chromatography (GPC) using as reference substances 9 kinds of polystyrenes having the weight-average molecular weights of 120,000, 52,000, 22,000, 9,200, 5,050, 2,950, 1,050, 580 and 162, respectively, and the latter is calculated therefrom. The above determination is carried out using GPC column KF804L×2 (manufactured by Showa Denko K.K.) and RI monitor L-3300 (manufactured by Hitachi Ltd.) with chloroform as a mobile phase.

Further, the biodegradable polymer having a free terminal carboxyl group is a biodegradable polymer in which the number-average molecular weight based on GPC measurement and the number-average molecular weight based on terminal group quantification almost agree with each other. The number-average molecular weight based on terminal group quantification is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide using phenolphthalein as an indicator while stirring at room temperature (20° C.) to determine the carboxyl group content; the number-average molecular weight based on terminal group quantification is calculated from the following equation:

Number-average molecular weight based on terminal group quantification=20000×A/B A: the mass (g) of the biodegradable polymer
B: the amount (ml) of 0.05 N alcoholic solution of potassium hydroxide added until the titration end point The number-average molecular weight based on terminal group quantification is an absolute value, while the number-average molecular weight based on GPC measurement is a relative value that varies depending on various analytical conditions (e.g., kind of mobile phase, kind of column, reference substance, slice width chosen, baseline chosen, etc.). Therefore, although it is difficult to express unequivocally and numerically, such description that "the number-average molecular weight based on GPC measurement and that based on terminal group quantification almost agree with each other" means, for example, that the number-average molecular weight based on terminal group quantification of a polymer synthesized from α-hydroxycarboxylic acids falls within the range from about 0.5 to about 2 times, preferably from about 0.7 to about 1.5 times as much as the number-average molecular weight based on GPC measurement.

For example, in case of a polymer having a free terminal carboxyl group and synthesized from one or more α-hydroxycarboxylic acids by catalyst-free dehydration polycondensation, the number-average molecular weight based on GPC measurement and the number-average molecular weight based on terminal group quantification almost agree with each other. On the other hand, in case of a polymer having substantially no free terminal carboxyl group and synthesized from a cyclic dimer by ring-opening polymerization using a catalyst, the number-average molecular weight based on terminal group quantification is significantly higher than (more than about 2 times) that based on GPC measurement. This difference makes it possible to clearly distinguish a polymer having a free terminal carboxyl group from a polymer having no free terminal carboxyl group.

The lactic acid/glycolic acid polymer having a free terminal carboxyl group can be produced by a per se known process, for example, that described in JP 61-28521 A (e.g., a process by a catalyst-free dehydration polycondensation reaction, or a dehydration polycondensation reaction in the presence of an inorganic solid acid catalyst, etc.).

While the decomposition/disappearance rate of the lactic acid/glycolic acid polymer varies widely, depending on the composition ratio or the weight-average molecular weight, the release duration can be extended (e.g., for about 6 months) by lowering the ratio of glycolic acid or increasing the molecular weight, since decomposition/disappearance is generally delayed as the ratio of glycolic acid decreases. In contrast, the release duration can be shortened (e.g., for about one week) by increasing the ratio of glycolic acid or decreasing the molecular weight. For obtaining a one week to two months type sustained-release preparation, it is preferable to use the lactic acid/glycolic acid polymer whose composition ratio and weight-average molecular weight are within the above-described ranges.

Therefore, the composition of the biodegradable polymer used in the present invention is preferably selected according to the desired kind of a bioactive peptide and the desired duration of sustained-release. Specifically, for example, when GH is used as the bioactive peptide, a lactic acid/glycolic acid polymer is preferably used. As the lactic acid/glycolic acid polymer, a preferred polymer is a lactic acid/glycolic acid copolymer having a lactic acid/glycolic acid composition ratio (mol %) of about 85/15 to about 50/50, more preferably about 75/25 to about 50/50. The weight-average molecular weight thereof is preferably about 8,000 to about 20,000, more preferably about 10,000 to about 20,000. Further, the degree of dispersion (weight-average molecular weight/number-average molecular weight) of the lactic acid/glycolic acid polymer is about 1.2 to about 4.0, more preferably about 1.5 to about 3.5.

The lactic acid/glycolic acid polymer used can be produced by known methods such as those described in the above publications and the like. The polymer is preferably that produced by catalyst-free dehydration polycondensation. Any organic solvent used for the production of the polymer and remaining in the polymer is removed after the polymerization. As a method for this purpose, there are, for example, heat drying, vacuum drying, flash drying with dried gas, etc. However, such a solvent can be much more quickly removed by contacting with continuously provided high-pressure gas according to the present invention, thereby significantly reducing the time required for removing the solvent. It is preferable to use the lactic acid/glycolic acid polymer (PLGA) wherein the number-average molecular weight based on terminal group quantification and the number-average molecular weight based on GPC measurement almost agree with each other.

Further, two kinds of lactic acid/glycolic acid polymers different in the composition ratio and/or the weight-average molecular weight may be used by mixing them in an arbitrary ratio. An example thereof is a mixture of a lactic acid/glycolic acid copolymer having the composition ratio of lactic acid/glycolic acid (mol %) of about 75/25 and the weight-average molecular weight of about 10,000, and a lactic acid/glycolic acid copolymer having the composition ratio of lactic acid/glycolic acid (mol %) of about 50/50 and the weight-average molecular weight is about 12,000. The preferred weight ratio of these copolymers upon mixing is about 25/75 to about 75/25.

The biodegradable polymer used in the present invention may be a metal salt of the above mentioned biodegradable polymer. For example, there can be used the various polyvalent metal salts of the biodegradable polymer described in WO97/01331, and the like. Preferably, a polyvalent metal salt of the lactic acid/glycolic acid polymer and the like, (more preferably, zinc salt, calcium salt, magnesium salt and the like, further more preferably zinc salt and the like) can be used. The species of the metal of the polyvalent metal salt is not specifically limited as long as it does not cause any adverse effect to a living body. For example, there can be used a polyvalent metal such as a divalent metal (e.g., iron, zinc, copper, calcium, magnesium, aluminum, tin, manganese and the like), a trivalent metal (e.g., iron, aluminum, manganese and the like), a tetravalent metal (e.g., tin and the like) and the like.

A metal salt of the biodegradable polymer is sometimes referred to as the biodegradable polymer herein inclusively. For example, in case of a polyvalent metal salt of the lactic acid/glycolic acid polymer, sometimes, it is also referred to as the lactic acid/glycolic acid polymer.

The above polyvalent metal salt of the biodegradable polymer can be produced by the method described in WO97/01331 or similar methods.

In case that a polyvalent metal salt of the biodegradable polymer is a zinc salt, it can be produced by reacting the biodegradable polymer with zinc oxide in an organic solvent.

In this method, first, a solution of the biodegradable polymer-zinc oxide complex in an organic solvent is prepared by coexistence of the biodegradable polymer with zinc oxide in the organic solvent. In that case, although the concentration of the biodegradable polymer in the solvent varies depending on the molecular weight thereof, a kind of the organic solvent and the like, for example, the concentration is about 0.1 to about 80% (W/W), preferably about 1 to about 70% (W/W), more preferably about 2 to about 60% (W/W). Further, although the amount of zinc oxide to be added varies depending on the kind of the organic solvent, for example, when the desired bioactive substance is a peptide, the amount is about 0.001 to about 2% (W/W), preferably about 0.01 to about 1.5% (W/W), more preferably about 0.1 to about 1% (W/W), when the desired bioactive substance is a non-peptide, the amount is about 0.001 to about 30% (W/W), preferably about 0.01 to about 20% (W/W), more preferably about 0.1 to about 10% (W/W), based on the amount of the biodegradable polymer, as described in JP 10-231252 A.

Regarding the order of the addition of the biodegradable polymer and zinc oxide to the organic solvent, zinc oxide in the form of a powder or suspended in the organic solvent can be added to a solution prepared by dissolving the biodegradable polymer in the organic solvent, or on the contrary, a solution of the biodegradable polymer in the organic solvent can be added to a suspension prepared by suspending zinc oxide in the organic solvent. Further, both of the biodegradable polymer and zinc oxide can be mixed in the form of powders, then the organic solvent can be added thereto. When the desired bioactive substance is a non-peptide, the organic solvent can be added after mixing of the biodegradable polymer, zinc oxide and the bioactive substance in the form of powders.

The content of the biodegradable polymer in the preparation of the present invention is generally about 30 to 99.9% (W/W), preferably about 60 to 97% (W/W), and more preferably about 70 to 90% (W/W).

The preparation of the present invention is produced by forming a solid material containing the bioactive substance and the biodegradable polymer and contacting the solid material with high-pressure gas.

The solid material containing the bioactive substance and the biodegradable polymer is formed by, when the bioactive substance is a bioactive peptide, for example, removing a solvent from a S/O dispersion obtained by dispersing a powder (S phase), which has been obtained by lyophilizing a solution of the bioactive peptide, in a solution of the biodegradable polymer in an organic solvent (O phase), or removing a solvent from a W/O emulsion obtained by dispersing an aqueous phase (W phase), which is an aqueous solution of the bioactive peptide, in a solution of the biodegradable polymer dissolved in an organic solvent, or removing a solvent from a solution of both bioactive peptide and biodegradable polymer dissolved in an organic solvent (O phase). As a method for this, there are, for example, (a) in-water drying method (S/O/W method and W/O/W or O/W method), (b) phase separation method (coacervation method) and (c) spray-drying method, or similar methods thereto and the like. In the present description, the solid material means a material in which constituents are linked to each other physically or chemically. The solid material includes, but not specifically limited to, microcapsules and the like.

The organic solvent used for dissolving the biodegradable polymer preferably has the boiling point of not lower than 30° C. Examples of the organic solvent includes halogenated hydrocarbons such as dichloromethane, dichloroethane, chloroform, carbon tetrachloride and the like, aliphatic hydrocarbons such as pentane, hexane, heptane, cyclohexane, petroleum benzine, petroleum ether and the like, aromatic hydrocarbons such as toluene, xylene and the like, alcohols such as methyl alcohol, ethyl alcohol, n-propyl alcohol, isopropyl alcohol, benzyl alcohol and the like, polyhydric alcohols such as ethylene glycol, propylene glycol and the like, esters such as methyl acetate, ethyl acetate and the like, organic acids such as formic acid, acetic acid, trifluoroacetic acid, trichloroacetic acid and the like, ethers such as diethyl ether, isopropyl ether, dioxane, tetrahydrofuran and the like, ketones such as acetone, methyl ethyl ketone and the like, nitrogen-containing compounds such as acetonitrile, propionitrile, pyridine, dimethylacetamide, dimethylformamide and the like, sulfur-containing compounds such as dimethylsulfoxide and the like, and the like. These may be mixed in a suitable ratio. A solvent contained in a substance, especially an organic compound, e.g., a medicament should be substantially removed from a product in view of properties of the medicament. Furthermore, for foods and general chemicals, residual solvents in products are strictly regulated depending on their application. The allowable amount of a residual solvent for medicaments is described in the guideline based on the ICH ("A guideline for residual solvent in medicament", Pharm. Tech. Japan 16(5), 687–704, 2000), and for example, the concentration limit for dichloromethane (classified into the Class 2) is 600 ppm, and the concentration limit for acetone (classified into the Class 3) is 0.5% (5,000 ppm).

Moreover, an organic solvent used in dissolution of the biodegradable polymer preferably has a boiling point of not higher than 120° C. The organic solvent includes such as halogenated hydrocarbons (e.g., dichloromethane, chloroform and the like), alcohols (e.g., ethanol, methanol and the like), ethyl acetate, acetonitrile and the like. These may be mixed in a suitable ratio. When an organic solvent is used alone, for example, dichloromethane, ethyl acetate, acetonitrile and the like are preferred. When organic solvents are used as a mixed solvent, for example, a combination of halogenated hydrocarbons (e.g., dichloromethane, chloroform and the like) and alcohols (e.g., ethanol, methanol and the like) or acetonitrile is preferred. The mixing ratio (volume ratio) of the halogenated hydrocarbons and alcohols or acetonitrile is about 100:1 to about 1:1, and it is desirable to use a mixed solvent having a mixing ratio of preferably about 30:1 to about 2:1. Furthermore, while the concentration of the biodegradable polymer in a solution varies depending on the molecular weight, the kind of an organic solvent, and the like, for example, it is about 0.01 to about 80% (W/W), preferably about 0.1 to about 70% (W/W), and more preferably about 1 to about 60% (W/W).

Hereinafter, a method for microcapsulation, in case of the production of sustained-release microcapsules as the preparation and using a bioactive peptide as the bioactive substance, will be explained in detail.

(a-1) In-Water Drying Method (S/O/W Method)

According to this method, first, a water-miscible organic solvent and/or a volatile salt are added to an aqueous solution of the bioactive peptide, and then, a bioactive peptide powder (S phase) is produced by lyophilization. A biodegradable polymer is dissolved in an organic solvent, and then, the above bioactive peptide powder is dispersed into the resulting organic solvent solution. The ratio (ratio by weight) of the bioactive peptide and the biodegradable polymer is, for example, about 1:1000 to about 1:1, preferably about 1:200 to about 1:5, more preferably about 1:100 to about 1:5. Preferably, an external physical energy is applied to disperse the bioactive peptide powder uniformly in the organic solvent solution. As a method for this, there can be used, for example, irradiation of ultrasonic wave, a turbine stirrer, a homogenizer and the like. As to the average particle size of the bioactive peptide in the organic solvent solution, it is preferably not more than about 10 μm, more preferably about 0.1 to 10 μm, further more preferably about 0.5 to 5 μm. In the present invention, the average particle size of the bioactive peptide means the value obtained by using a laser analytic particle size distribution measuring device (SALD2000A, manufactured by Shimadzu Corporation) after dispersing the bioactive peptide in an organic solvent such as dichloromethane by using a homogenizer. In this process, the bioactive peptide is added to the organic solvent at the concentration of about 20 to 100 mg/ml, and then dispersed using a homogenizer, such as Polytron (manufactured by Kinematica) at about 20,000 rpm for about 30 seconds to 1 minutes. The dispersion is diluted appropriately with the organic solvent so that the average particle size can be measured with the above particle size distribution measuring device, followed by analysis.

Then, the organic solvent dispersion (S/O dispersion) thus prepared is added to an aqueous solvent (W phase), and then the same external physical energy as that mentioned above, for example, irradiation of ultrasonic wave, a turbine stirrer, a homogenizer and the like is applied to form a S/O/W emulsion. Then, the organic solvent of O phase is evaporated to produce microcapsules. At this time, the volume of the aqueous phase is generally selected from about 1 times to about 10,000 times, preferably about 2 times to about 5,000 times, more preferably about 5 times to about 2,000 times as much as the volume of the O phase.

An emulsifier can be added to the above external aqueous phase. As the emulsifier, there can be used any one which is generally capable of forming a stable S/O/W emulsion. Examples of the emulsifier include anionic surfactants, nonionic surfactants, polyoxyethylene castor oil derivative, polyvinylpyrrolidones, polyvinyl alcohols, carboxymethylcelluloses, lecithin, gelatin, hyaluronic acids and the like. These emulsifiers can be used by appropriately combining them. The concentration of the emulsifier in the external aqueous phase is, preferably about 0.001% to 20% (w/w), more preferably about 0.01% to 10% (w/w), particularly preferably about 0.05% to 5% (w/w).

The thus-obtained microcapsules are recovered by centrifugation or filtration, washed with distilled water to remove the emulsifier and the like adhering to the surface of microcapsules, re-dispersed in distilled water, and lyophilized.

In the present invention, examples of the water-miscible organic solvent, which can be added to the aqueous solution of the bioactive peptide, include alcohols (e.g. methanol, ethanol, isopropanol and the like, preferably methanol, ethanol and the like), acetone and the like. These may be used by mixing them at an appropriate ratio. Preferably, an alcohol, more preferably ethanol is used alone. The amount (concentration) to be added to the aqueous solution of the bioactive peptide is about 0.03 to 0.5% (V/V), preferably about 0.06 to 0.25% (V/V); more preferably about 0.1 to 0.15% (V/V), in terms of volume-ratio. By further lyophilizing the resultant aqueous solution of the bioactive peptide obtained by addition of the water-miscible organic solvent, it is possible to prepare a bioactive peptide powder which is easy to handle (superior operability) and is very fine (a small particle size).

In the present invention, as the volatile salt, which is added to the aqueous solution of the bioactive peptide, there are, for example, ammonium salts (e.g., ammonium acetate, ammonium bicarbonate, ammonium carbonate, ammonium chloride and the like, preferably ammonium acetate and the like). The volatile salt can be used by mixing them at an appropriate ratio. The added amount of the volatile salt is about 10 times to about 80 times mole, preferably about 10 times to about 70 times mole, more preferably about 15 times to about 70 times mole, further more preferably about 20 times to about 70 times mole, most preferably about 20 times to about 50 times mole as much as the aqueous solution of the bioactive peptide in terms of mole ratio. By lyophilizing the resultant aqueous solution of the bioactive peptide obtained by addition of the volatile salt in a similar manner as the addition of the water-miscible organic solvent, it is possible to prepare the bioactive peptide powder which is easy to handle (superior operability) and is very fine (a small particle size).

In the present invention, the water-miscible organic solvent and/or the volatile salt added to the aqueous solution of the bioactive peptide can be used alone or in appropriate combination thereof. When the water-miscible organic solvent and the volatile salt are used in combination thereof, they can be added to the aqueous solution of the bioactive peptide in accordance with the above amounts respectively.

(a-2) In-water Drying Method (W/O/W Method)

According to this method, water or a suitable buffer is added to the bioactive peptide to give a solution of the bioactive peptide (W phase). The biodegradable polymer is then dissolved in an organic solvent, and to this organic solvent solution is added the above-mentioned solution of the bioactive peptide and the mixture is dispersed. The thus-obtained W/O emulsion is added to an aqueous solvent (W phase). According to the same method as the above-mentioned S/O/W method, microcapsules are obtained through a W/O/W emulsion.

(a-3) In-water Drying Method (O/W Method)

According to this method, the biodegradable polymer together with the bioactive peptide are dissolved in an organic solvent. The organic solvent (O phase) is then added to an aqueous solvent (W phase). According to the same method as the above-mentioned S/O/W method, microcapsules are obtained through an O/W emulsion.

(b) Phase Separation Method (Coacervation Method)

According to this method, a coacervating agent is gradually added to the S/O dispersion of (a-1) or the W/O emulsion of (a-2) or the O phase solution of (a-3) as described above with stirring to precipitate and solidify microcapsules. The amount of the coacervating agent to be added is about 0.01 to about 1,000 times by volume, preferably about 0.05 to about 500 times by volume, especially preferably about 0.1 to about 200 times by volume as much as the volume of the above dispersion. Any coacervating agent can be used, as long as it is a polymeric, mineral oil or vegetable oil compound which is miscible with the organic solvent used for dissolution of the biodegradable polymer but does not dissolve the biodegradable polymer used. Specifically, examples of the coacervating agent include silicone oil, sesame oil, soybean oil, corn oil, cottonseed oil, coconut oil, linseed oil, mineral oil, n-hexane, n-heptane and the like. Two or more of these can be used in combination. The thus-obtained microcapsules are recovered by filtration, washed repeatedly with heptane and the like to remove the coacervating agent. Further, washing is carried out in the same manner as that in the above (a), followed by lyophilization.

In the production of microcapsules by the in-water drying method or coacervation method, an antiaggregation agent can be added for preventing aggregation of particles. Examples of the antiaggregation agent can be used, for example, water-soluble polysaccharides such as mannitol, lactose, glucose, starches (e.g., corn starch and the like), hyaluronic acid and its alakaline metal salt, etc.; protein such as glycine, fibrin, collagen, etc.; inorganic salts such as sodium chloride, sodium hydrogen phosphate, etc.; and the like.

(c) Spray-Drying Method

In this method, microcapsules are produced by spraying the S/O dispersion of (a-1), the W/O emulsion of (a-2) or the O phase solution of (a-3) described above via a nozzle into the drying chamber of a spray drier to volatilize the organic solvent in fine droplets within a very short time. As the nozzle, there are, for example, a two-fluid nozzle type, a pressure nozzle type and a rotary disc type and the like. It is also advantageous, if necessary, to spray an aqueous solution of the above-described antiaggregation agent via another nozzle in order to prevent aggregation of microcapsule particles.

The solid material formed by the above-mentioned method such as microcapsules containing the bioactive substance and the biodegradable polymer, and the like, is then contacted with high-pressure gas (preferably carbon dioxide) to further extract and remove the organic solvent.

Specifically, for example, a lyophilized microcapsule powder obtained by (a) is fed into an extraction vessel, and extraction treatment is carried out with an extraction system comprising a carbon dioxide delivery pump and a pressure regulating valve. Alternatively, a microcapsule suspension before lyophilization, obtained by (a) or (b) may be fed into an extraction vessel and subjected to extraction treatment similarly. In these cases, the extraction treatment is desirably carried out under more gentle conditions so as to not deteriorate the quality of a sustained-release preparation.

The high-pressure gas in the present invention is gas at pressure not less than the atmospheric pressure at a given temperature but not more than the liquefying pressure at said temperature.

Examples of the high-pressure gas used in the present invention include carbon dioxide, nitrous oxide, nitrogen, helium, argon, alkane (e.g., ethane, propane and the like), alkene (e.g., ethylene and the like), and the like. While these may be used by mixing them in a suitable ratio, preferably, it is desirable to use carbon dioxide alone.

When a temperature of high-pressure gas contacting with a preparation is much higher than the glass transition temperature of a biodegradable polymer used as a substrate of the preparation, the risk of adhesion, deformation, decomposition of the bioactive substance, deterioration and the like of the preparation increases. The glass transition temperature in the present invention means medium glass transition temperature obtained by rising temperature at the rate of 10 or 20° C./min using a differential scanning calorimeter (DSC). Alternatively, when a temperature of high-pressure gas is too low, the removal of an organic solvent becomes insufficient. The organic solvent is preferably removed to less than 1,000 ppm, preferably less than 500 ppm, and more preferably less than 100 ppm. Therefore, the advantageous temperature for using carbon dioxide as high-pressure gas in the present invention is within a temperature range of +20 to −60° C., preferably +10 to −50° C., more preferably 0 to −40° C., still more preferably −5 to −30° C., and the most preferably −10 to −25° C., based on the glass transition temperature of the biodegradable polymer (generally about 20 to 60° C.).

While the range of pressure varies depending on the selected high-pressure gas, but generally, when the pressure of high-pressure gas is too high, the risk of adhesion, deformation, increase of the initial release immediately after administration and the like for the microcapsules increases, or when the pressure is too low, the removal of the organic solvent becomes insufficient. The advantageous pressure for using carbon dioxide as high-pressure gas in the present invention pressure is about 1 to 7 MPa, preferably about 1 to 4 MPa, and more preferably about 2 to 4 MPa.

While the period for contacting with the high-pressure gas varies depending on the pressure of the high-pressure gas, temperature, the amount of microcapsules to be treated and the like, it is preferably about 5 minutes to about 48 hours when carbon dioxide is used as high-pressure gas. More preferably, it is about 10 minutes to about 12 hours.

Hereinafter the step for high-pressure gas treatment of microcapsules using carbon dioxide in a high-pressure gaseous state will be explained in more detail with referring to FIG. 1. FIG. 1 is a schematic drawing, which exemplifies an apparatus used for the high-pressure gas treatment in the present invention. Such apparatus for high-pressure gas treatment comprises, for example, as shown in FIG. 1, a liquefied carbon dioxide bomb 1, a carbon dioxide delivery pump 2, a heat exchanger 3, an extraction vessel 4, a thermostat 5, a detector 6, an automatic pressure-regulating valve 7 and a recovery vessel 8. Microcapsules to be treated are fed into the extraction vessel 4, and the apparatus is sealed and heated to a predetermined temperature. The liquefied carbon dioxide is then delivered from the liquefied carbon dioxide bomb 1 to the heat exchanger 3 by the carbon dioxide delivery pump 2, heated to a predetermined temperature, and converted into a high-pressure gaseous state. The carbon dioxide in the high-pressure gaseous state is then blown into the extraction vessel 4 to dissolve and extract the solvent in the microcapsules into the high-pressure gas. The extracted solvent is recovered in the recovery vessel 8 via the detector 6 and automatic pressure regulating valve 7. The pressure applied to the whole system is controlled by the automatic pressure regulating valve 7 connected to the lowest downstream. By contacting with the high-pressure gas for a given period, the excess amount of the initial release of the bioactive substance immediately after administration is markedly suppressed, and the residual organic solvent can be removed without producing aggregates, related substances or reactants of the bioactive peptide.

The sustained-release preparation of the present invention is preferably in the form of fine particles. That is, the sustained-release preparation does not provide undue pain to a patient, when it is administered to said patient using an injection needle, which is generally used for subcutaneous or intramuscular injection. The particle size of the sustained-release preparation is, for example, about 0.1 to 300 µm, preferably about 1 to 150 µm, specifically preferably about 2 to 100 µm in terms of a mean particle diameter. The content of the bioactive substance contained in the sustained-release preparation of the present invention is, for example, in case of a bioactive peptide, generally about 0.1 to 50% (W/W), preferably about 0.2 to 30% (W/W), and more preferably about 0.5 to 20% (W/W). The content of the biodegradable polymer contained in the sustained-release preparation of the present invention is generally about 30 to 99.9% (W/W), preferably about 60 to 97% (W/W), and more preferably about 70 to 90% (W/W).

The initial release percentage of the sustained-release preparation of the present invention [the release percentage up to one day (24 hours) after administration] is, in case of a bioactive peptide, preferably about not more than 40%, more preferably about 1 to 40%, and more preferably about 3 to 35%.

The sustained-release preparation of the present invention can be administered as microcapsules or as preparations in various forms prepared by using microcapsules as a raw material, such as parenteral preparations (e.g., injectable preparations or preparations for implantation in muscle, subcutaneous, organs and the like, preparations for administering to mucosa onto cavitas nasi, rectum, uterus, etc.), oral preparations (e.g., capsules (hard capsules, soft capsules, etc.), solid preparations such as granules and powders, etc., liquid preparations such as suspensions, etc.), and the like.

In particular, the sustained-release preparation of the present invention is preferably for injection. For example, in case that the sustained-release preparation is microcapsules, it is possible to obtain a practical sustained-release preparation for injection by formulating the microcapsules in an aqueous suspension together with a dispersing agent (e.g., a surfactant such as Tween 80, HCO-60, etc., polysaccharides such as carboxymethyl celluloses, sodium alginate, hyaluronic acid, etc.), a preservative (e.g., methylparaben, propylparaben, etc.), a tonicity agent (e.g., sodium chloride, mannitol, sorbitol, glucose, etc.), and the like. It is also possible to obtain a practical sustained-release preparation for injection by dispersing the microcapsules together with a vegetable oil such as sesame oil, corn oil, etc., or a mixture thereof with a phospholipid such as lecithin, or a medium-chain fatty acid triglyceride (e.g., Miglyol 812) to prepare an oily suspension.

When the sustained-release preparation is, for example, microcapsules, the particle size of the sustained-release preparation for an injectable suspension can be selected from the range satisfying the requirements for the degree of dispersion and the needle passability for the injection. For example, the particle size is within the range of about 0.1 to about 300 μm, preferably about 1 to about 150 μm, more preferably about 2 to about 100 μm, as the average particle size.

Methods for producing a sterile preparation from the above microcapsules include, but are not limited to, to carry out entire production steps aseptically, to sterilize with gamma rays, to add an antiseptic, and the like.

The sustained-release preparation can be safely used in mammals (e.g., human, cattle, pig, dog, cat, mouse, rat, rabbit and the like) with low toxicity.

Indication of the sustained-release preparation varies depending on a bioactive peptide used. The sustained-release preparation is useful to prevent or treat diabetes when insulin is used as the bioactive peptide; viral hepatitis (e.g., type C hepatitis, HBe antigen-positive active hepatitis and the like) and cancer (e.g., renal carcinoma, multiple myeloma and the like) when interferon-α is used; anemia (e.g., anemia during dialysis of kidney and the like) when erythropoietin is used; neutropenia (e.g., in cancer therapy and the like) and infections when G-CSF is used; cancer (e.g., hemangioendothelioma and the like) when IL-2 is used; fracture, wound (e.g., bedsore and the like), periodontitis and gastrointestinal ulcer when FGF is used; thrombocytopenia when FGF-9 is used; senile dementia and neuropathy when NGF is used; thrombosis when TPA is used; and cancer when tumor necrosis factor is used. Further, the sustained-release preparation containing GH is applied to Turner's syndrome, chronic renal diseases, achondroplasia, and adult hypopituitarisin (adult GHD), in addition to pituitary dwarfism, based on growth hormone activity of GH. Further, since, GH is reported to be applied to diseases such as Down syndrome, Silver syndrome, hypochondroplasia and juvenile chronic arthritis to provide excellent therapeutic effects, the sustained-release preparation containing GH can also be applied to these diseases. The sustained-release preparation containing GH is also useful to prevent or treat congestive heart-failure and the like. The other indications to which the sustained-release preparation containing GH can be applied include, hematogenesis during organ implantation or treatment for a patient suffering from AIDS with a drug, improvement of hypoalimentation, renal anemia, angina pectoris, hyperlipidemia, obesity, acceleration of treatment for burn, wound or ulcer, invasiveness from surgery (operation, lesion), early recovery after operation, sepsis, prevention of fracture due to osteoporosis, early recovery of muscular strength of a patient suffering from fracture due to osteoporosis, amyotropic lateral scelosis (ALS), decubitus and the like. Furthermore, it is expected to have effects as an antiaging agent aiming at improving the quality of life (QOL) for frail aged persons, or effects for suppressing the development or improving neurodegenerative diseases (Alzheimer's disease, Parkinson's disease, cerebrovascular disease and the like) due to the nerve protective effect of hGH. By forming GH into a sustained-release preparation, drug effects superior to those of a GH subcutaneous injection can be obtained for these indications. When the bioactive substance is candesartan, the preparation is effective for the prevention or improvement of cardiomegaly, cardiac failure, myocardial infarct, cerebral stroke, ischemic peripheral neuropathy, myocardial ischemia, venous incompetence, development of cardiac failure after myocardial infarct, diabetic nephropathy, nephritis, glomerular nephritis, arteriosclerosis, vascular hypertrophy, vascular hypertrophy or occulusion after percutaneous transluminal coronary angioplasty, vascular re-occulusion after bypass operation, hyperaldosteronism, glomerular sclerosis, renal failure, glaucoma, ocular hypertension, hyperlipidemia, stenocardia, aneurysm, coronary arteriosclerosis, cerebral arteriosclerosis, peripheral arteriosclerosis, thrombosis, central nerve system disease, Alzheimer's disease, amnesia, depression, amnestic syndrome, senile dementia, dysesthesia, multiple organ failure, prevention or treatment of disease or sclerodermia associated with endothelial disorder, or symptom of anxiety, symptom of strain, unpleasantmental state or maldigestion.

Although the dose of the sustained-release preparation varies depending on a particular kind and amount of the bioactive peptide, release duration, target disease, subject animal species and other factors, it can be set at any level, as long as an effective concentration of the bioactive peptide in the body is maintained. For example, when the sustained-release preparation is one designed for two week release, the dose of the bioactive peptide can be suitably chosen from the range of preferably about 0.0001 to about 10 mg/kg body weight, more preferably about 0.05 to about 3 mg/kg body weight, per an adult. The preferred administration frequency of the sustained-release preparation can be suitably chosen from once a week, once every two weeks, once a month, once every two months and the like, depending on a particular kind and amount of the bioactive peptide, dosage form, release duration, target disease, subject animal species and other factors. Preferably, the sustained-release preparation includes a one week to two months type sustained-release preparation, more preferably one week to one month type sustained-release preparation.

When the bioactive peptide as an active component in the sustained-release preparation is, for example, insulin, the dose per administration to an diabetic adult is suitably chosen from the range of usually about 0.001 to about 1 mg/kg body weight, preferably about 0.01 to about 0.2 mg/kg body weight, as an effective ingredient. And the preferred administration frequency is once a week.

When the bioactive peptide as an active component in the sustained-release preparation is GH, the dose can be set at any level, as long as an effective concentration of GH in the body is maintained, although varying depending on a particular kind and amount of GH, release duration, target disease, subject animal species and other factors. Regarding the treatment of the above described diseases, when the sustained-release preparation is one designed for two week release, the dose of GH can be suitably chosen from the range of about 0.01 to about 5 mg/kg body weight (about 0.03 to about 15 IU/kg body weight), more preferably about 0.05 to about 1 mg/kg body weight (about 0.15 to about 3 IU/kg body weight), per a child or an adult for safe administration. The preferred administration frequency can be suitably chosen from once a week, once every two weeks, once a month and etc., depending on a particular amount of GH, dosage form, release duration, target disease, subject animal species and other factors, preferably one week to two months-type sustained-release preparation, more preferably one week to one month-type sustained-release preparation.

The sustained-release preparation is preferably stored at ordinary temperature or in a cold place. More preferably, the sustained-release preparation is stored in a cold place. The "ordinary temperature" and the "cold place" are defined in the Pharmacopoeia of Japan. Namely, the "ordinary temperature" means 15 to 25° C., and the "cold place" means a temperature of not more than 15° C. In the "cold place", it is more preferably about 2 to 8° C.

Hereinafter the present invention will be explained more specifically with referring to the Reference Examples, Examples and Test Examples, which do not limit the present invention.

REFERENCE EXAMPLE 1

To an aqueous solution of gene recombinant hGH (final hGH concentration=2 mg/ml) was added ammonium acetate (20-fold mol equivalent). The mixture (100 ml) was dropwise added to the inner wall surface of a distillation flask cooled in a dry ice-ethanol bath using a peristaltic pump over 30 minutes to rapid-freeze the mixture and the frozen mixture was dried in vacuo to obtain hGH powder. A lactic acid-glycolic acid copolymer (lactic acid/glycolic acid=65/35, viscosity=0.160 dl/g, 1.690 g) and zinc oxide (10 mg) were dissolved in dichloromethane (2.7 ml). To the organic solvent solution was added the above-mentioned hGH powder (359 mg) and the mixture was finely granulated with Polytron (manufactured by Kinematica). This S/O dispersion was added to a 0.1% aqueous solution of polyvinyl alcohol (800 ml) and the mixture was stirred and emulsified using a homomixer. The mixture was stirred at room temperature for 3 hours to volatilize dichloromethane and centrifuged (about 1,500 rpm) to obtained microcapsules. The microcapsules were then washed twice with distilled water (400 ml) and lyophilized from D-mannitol (0.2 g) to obtain lyophilized hGH-containing microcapsule powder. Under the same conditions, six batches of the microcapsules were produced. The yield of the lyophilized microcapsule powder obtained was 6.8 g.

REFERENCE EXAMPLE 2

To an aqueous solution of gene recombinant hGH (final hGH concentration=2 mg/ml) was added ammonium acetate (20-fold mol equivalent). A lactic acid-glycolic acid copolymer (lactic acid/glycolic acid=50/50, viscosity=0.154 dl/g, 1.850 g) and zinc oxide (10 mg) were dissolved in dichloromethane (2.7 ml). To the organic solvent solution was added the above-mentioned hGH powder (155 mg) and the mixture was finely granulated with Polytron (manufactured by Kinematica). This S/O dispersion was added to a 0.1% aqueous solution of polyvinyl alcohol (800 ml) and the mixture was stirred and emulsified using a homomixer. The mixture was stirred at room temperature for 3 hours to volatilize dichloromethane and centrifuged (about 1,500 rpm) to obtain microcapsules. The microcapsules were then washed twice with distilled water (400 ml) and lyophilized from D-mannitol (0.2 g) to obtain lyophilized hGH-containing microcapsule powder. Under the same conditions, six batches of the microcapsules were produced. The yield of the lyophilized microcapsule powder obtained was 7.6 g.

REFERENCE EXAMPLE 3

To an aqueous solution of gene recombinant hGH (final hGH concentration=2 mg/ml) was added ammonium acetate (20-fold mol equivalent). The mixture (100 ml) was dropwise added to the inner wall surface of a distillation flask cooled in a dry ice-ethanol bath using a peristaltic pump over 30 minutes so as to rapid-freeze the mixture and the frozen mixture was dried in vacuo to obtain hGH powder. A lactic acid-glycolic acid copolymer (lactic acid/glycolic acid=65/35, viscosity=0.160 dl/g, 1.521 g) and zinc oxide (9 mg) were dissolved in dichloromethane (2.4 ml). To the organic solvent solution was added the above-mentioned hGH powder (270 mg) and the mixture was finely granulated with Polytron (manufactured by Kinematica). This S/O dispersion was added to a 0.1% aqueous solution of polyvinyl alcohol (800 ml) that had been cooled to 18° C., and the mixture was stirred and emulsified using a homomixer. The mixture was stirred at room temperature for 3 hours to volatilize dichloromethane and centrifuged (about 1,500 rpm) to obtain microcapsules. To the microcapsule suspension, which had been obtained by removing the supernatant as much as possible by aspiration operation, was added a 50% aqueous solution of ethanol (500 ml), and the mixture was stirred gently using a propeller at room temperature for 15 minutes. The mixture was centrifuged (about 1,500 rpm) to obtain microcapsules. The microcapsules were then washed twice with distilled water (400 ml) and lyophilized from D-mannitol (180 mg) to give lyophilized hGH-containing microcapsule powder. In order to remove the residual solvent, the powder was dried in vacuo at 46° C. for 72 hours to obtain microcapsules.

REFERENCE EXAMPLE 4

Evaluation of Pharmacological Effect for Human Growth Hormone-containing Microcapsules To female SD rats, which had been removed glandula pituitaria at four-week old, was administered an immunosuppressive agent, tacrolimus (Prograf injection, manufactured by Fujisawa Pharmaceutical Co., Ltd.) to suppress the production of antibodies to hGH. Microcapsules were administered to the animal at six-week old, and the body weight, body length and concentration of rat insulin-like growth factor I (rIGF-I) in blood serum were measured for 5 weeks. Specifically, the Prograf injection (5 mg) was diluted with saline, and the dilution was injected subcutaneously, at the dose of 50 µg/0.2 ml/rat at three days before the first administration of microcapsules, immediately after the first administration of microcapsules and on the 4th, 7th and 11th days after the first administration, and at the dose of 75 µg/0.2 ml/rat on the 14th, 18th, 21st, 25th, 28th and 32nd days after the first administration, respectively. Furthermore, in order to more physically normalize the glandula pituitaria-removed rat, hormone supplementation was also carried out. A mixed solution of sodium L-thyroxin pentahydrate and hydrocortisone succinate (both are manufactured by Wako pure chemical Industries, Ltd) (the final concentrations were 1 µg and 50 µg per 0.2 ml/rat, respectively) was subcutaneously administered three times a week, namely, three days before the first administration of the microcapsules, immediately after the first administration, and on the 2nd, 4th, 7th, 9th, 11th, 14th, 16th, 18th, 21st, 23rd, 25th, 28th, 30th and 32nd days after the first administration. The microcapsules were dispersed in a dispersion medium (5% mannitol, 0.5% carboxymethylcellulose sodium, 0.1% Tween 80) so as to be 24 mg hGH/ml, and 0.5 ml of the dispersion was administered subcutaneously to the back of the rat under ether anesthesia. The dose was 12 mg as hGH. After the administration of microcapsules, the body weight and body length of the rat was measured with time up to 35 days. In addition, blood was collected from the caudal vein with time and blood serum was fractionated. The concentration of rIGF-I in blood serum was measured by radioimmunoassay (DSL-2900, Diagnostic Systems Laboratories, Inc.).

REFERENCE EXAMPLE 5

Candesartan (2.0 g), zinc oxide (manufactured by Hakusui Chemical Industries, Ltd., 0.37 g) and a lactic acid-glycolic acid copolymer (lactic acid/glycolic acid 75/25 (mol %), weight-average molecular weight 8,700, manufactured by Wako Pure Chemical Industries, Ltd, 3.6 g) were added to a mixed solution of dichloromethane (12.75 ml), methanol (2.25 ml) and acetic acid (0.136 ml), and the mixture was stirred with shaking at room temperature overnight to obtain a homogenous solution. The solution was added to a 0.1% aqueous solution of polyvinyl alcohol (800 ml) containing 20 mM of zinc acetate, which had been previously adjusted to 18° C., and an O/W emulsion was prepared using a turbine type homomixer at 7,000 rpm. This O/W emulsion was stirred at room temperature for 3 hours to volatilize dichloromethane, methanol and acetic acid, and the oil phase was solidified and collected using centrifuge at 3,000 rpm. This was dispersed in distilled water again and further centrifuged to wash out free drug and the like. The collected microcapsules were dispersed again by adding distilled water containing mannitol (0.8 g) and lyophilized to obtain a powder. The encapsulation ratio of candesartan in microcapsules was 90.9%, and the content of candesartan in microcapsules/mannitol powder was 26.5%.

REFERENCE EXAMPLE 6

One batch was conducted in the following amount for treatment. Candesartan (2.0 g), zinc oxide (manufactured by Hakusui Chemical Industries, Ltd., 0.37 g) and a lactic acid-glycolic acid copolymer (lactic acid/glycolic acid 75/25 (mol %), weight-average molecular weight 8,700, manufactured by Wako Pure Chemical Industries, Ltd, 3.6 g) were added to a mixed solution of dichloromethane (12.75 ml), methanol (2.25 ml) and acetic acid (0.136 ml), and the mixture was stirred with shaking at room temperature overnight to obtain a homogenous solution. The solution was added to a 0.1% aqueous solution of polyvinyl alcohol (800 ml) containing 10 mM of zinc acetate, which had been previously adjusted to 18° C., and an O/W emulsion was prepared using a turbine type homomixer at 7,000 rpm. This O/W emulsion was stirred at room temperature for 3 hours to volatilize dichloromethane, methanol and acetic acid, and the oil phase was solidified and collected using centrifuge at 3,000 rpm. This was dispersed in distilled water again and further centrifuged to wash out free drug and the like. The above-mentioned operations were conducted by two batches, and the microcapsules of the two batches were mixed, and the microcapsules were dispersed again by adding distilled water containing mannitol (1.6 g) and lyophilized to obtain a powder. The encapsulation ratio of candesartan in microcapsules was 90.7%, and the content of candesartan in microcapsules/mannitol powder was 26.4%.

EXAMPLE 1

The solvent was removed under the following four conditions using 0.3 g of the hGH-containing lyophilized microcapsule powder obtained in Reference Example 1, respectively. The microcapsule powder was transferred into an extraction vessel (volume 10 ml) of a supercritical fluid extraction apparatus (manufactured by JASCO Corporation). The apparatus was sealed and heated to a predetermined temperature in a thermostat. Carbon dioxide was delivered to a heat exchanger via a delivery pump (SCF-Get) at the bomb pressure (about 6 to 7 MPa) and heated to the given temperature. The pressure applied to the whole system was controlled by an automatic pressure regulating valve (SCF-Bpg), and the carbon dioxide was converted into a high-pressure gaseous state at given pressure. The high-pressurized carbon dioxide gas was then blown into an extraction vessel, and the solvent was removed under the following four conditions.
(1) Pressure 2 MPa, temperature 15° C., extraction period 15 minutes.
(2) Pressure 2 MPa, temperature 15° C., extraction period 30 minutes.
(3) Pressure 2 MPa, temperature 15° C., extraction period 45 minutes.
(4) Pressure 2 MPa, temperature 15° C., extraction period 60 minutes.

EXAMPLE 2

The solvent was removed under the following four conditions using 0.3 g of the hGH-containing lyophilized microcapsule powder obtained in Reference Example 2, respectively. The microcapsule powder was transferred into an extraction vessel (volume 10 ml) of a supercritical fluid extraction apparatus (manufactured by JASCO Corporation). The apparatus was sealed and heated to a given temperature in a thermostat. Carbon dioxide was delivered to a heat exchanger via a delivery pump (SCF-Get) at the bomb pressure (about 6 to 7 MPa) and heated to the predetermined temperature. The pressure applied to the whole system was controlled by an automatic pressure regulating valve (SCF-Bpg), and the carbon dioxide was converted into a high-pressure gaseous state at predetermined pressure. The high-pressurized carbon dioxide gas was then blown into an extraction vessel, and the solvent was removed under the following four conditions.
(1) Pressure 2 MPa, temperature 15° C., extraction period 30 minutes.
(2) Pressure 2 MPa, temperature 15° C., extraction period 60 minutes.
(3) Pressure 2 MPa, temperature 15° C., extraction period 180 minutes.
(4) Pressure 1 MPa, temperature 150° C., extraction period 720 minutes.

EXAMPLE 3

The solvent was removed under the following 18 conditions using 0.3 g of the candesartan-containing lyophilized microcapsule powder obtained in Reference Example 5, respectively. The microcapsule powder was transferred into an extraction vessel (volume 10 ml) of a supercritical fluid extraction apparatus (manufactured by JASCO Corporation). The apparatus was sealed and heated to a predetermined temperature using a thermostat. Carbon dioxide was delivered to a heat exchanger via a delivery pump (SCF-Get) at the bomb pressure (about 6 to 7 MPa) and heated to the given temperature. The pressure applied to the whole system was controlled by an automatic pressure regulating valve (SCF-Bpg), and the carbon dioxide was converted into a high-pressure gaseous at the given pressure. The high-pressurized carbon dioxide gas was then blown into an extraction vessel, and the solvent was removed under the following 18 conditions.
(1) Pressure 2.0 MPa, temperature 15° C., extraction period 30 minutes.
(2) Pressure 2.0 MPa, temperature 15° C., extraction period 60 minutes.
(3) Pressure 2.0 MPa, temperature 15° C., extraction period 120 minutes.
(4) Pressure 2.0 MPa, temperature 15° C., extraction period 180 minutes.
(5) Pressure 2.5 MPa, temperature 15° C., extraction period 30 minutes.
(6) Pressure 2.5 MPa, temperature 15° C., extraction period 60 minutes.
(7) Pressure 2.5 MPa, temperature 15° C., extraction period 120 minutes.
(8) Pressure 2.5 MPa, temperature 15° C., extraction period 180 minutes.
(9) Pressure 3.0 MPa, temperature 15° C., extraction period 15 minutes.
(10) Pressure 3.0 MPa, temperature 15° C., extraction period 30 minutes.
(11) Pressure 3.0 MPa, temperature 15° C., extraction period 60 minutes.
(12) Pressure 3.0 MPa, temperature 15° C., extraction period 120 minutes.
(13) Pressure 3.0 MPa, temperature 15° C., extraction period 180 minutes.
(14) Pressure 3.5 MPa, temperature 15° C., extraction period 30 minutes.
(15) Pressure 3.5 MPa, temperature 15° C., extraction period 60 minutes.
(16) Pressure 3.5 MPa, temperature 15° C., extraction period 120 minutes.
(17) Pressure 3.5 MPa, temperature 15° C., extraction period 180 minutes.
(18) Pressure 4.0 MPa, temperature 15° C., extraction period 30 minutes.

EXAMPLE 4

The solvent was removed under the following three conditions using the candesartan-containing lyophilized microcapsule powder obtained in Reference Example 6, respectively. The microcapsule powder was transferred into an extraction vessel (volume 10 ml) of a supercritical fluid extraction apparatus (manufactured by JASCO Corporation). The apparatus was sealed and heated to a predetermined temperature using a thermostat. Carbon dioxide was delivered to a heat exchanger via a delivery pump (SCF-Get) at the bomb pressure (about 6 to 7 MPa) and heated to a given temperature. The pressure applied to the whole system was controlled by an automatic pressure regulating valve (SCF-Bpg), and the carbon dioxide was converted into a high-pressure gaseous state at a given pressure. The high-pressurized carbon dioxide gas was then blown into an extraction vessel, and the solvent was removed under the following three conditions.
(1) pressure 3.0 MPa, temperature 15° C., extraction period 60 minutes, charged amount of the microcapsules 0.3 g.
(2) pressure 3.0 MPa, temperature 15° C., extraction period 60 minutes, charged amount of the microcapsules 2 g.
(3) pressure 3.0 MPa, temperature 15° C., extraction period 60 minutes, charged amount of the microcapsules 5 g.

TEST EXAMPLE 1

For the hGH-containing microcapsules and untreated lyophilized microcapsules obtained in Example 1 (1) to (4), the amount of residual dichloromethane (DCM) and hGH content in the microcapsules were measured by the following method.

(1) Amount of Residual Dichloromethane (DCM)

Microcapsules (about 100 mg) were weighed precisely, dissolved in dimethylsulfoxide and made up to exactly 5 ml to prepare a sample solution. Separately, dichloromethane (about 1 g) was weighed precisely and made up to exactly 20 ml with addition of dimethylsulfoxide. This solution was diluted by exactly 10000 times with dimethylsulfoxide to obtain a standardized solution. The sample solution and standardized solution (each 1 µl) were tested by gas chromatography under the following conditions, and the peak area of dichloromethane for each solution was measured by automatic integration to calculate the amount of dichloromethane.
Detector: hydrogen flame ionization detector
Column: OVI-G43 film thickness 3 µm, 0.53 mm i.d.×30 m (Supelco)
Inlet temperature: 140° C.
Detector temperature: 260° C.
Column temperature: 40° C. (10 min retention)→240° C. (35° C./min)→240° C. (20 min retention)→cooling→40° C.
Carrier gas: helium
Flow: 35 cm/sec (2) hGH Content Microcapsule (10 mg) was weighed precisely in a 5 ml messflask, acetonitrile (1.75 ml) was added thereto and the mixture was ultra-sonicated. To the obtained acetonitrile solution was added 150 mM phosphate saline buffer (pH 8.0, 3 ml), and the solution was ultra-sonicated and made up to a given volume with 150 mM phosphate saline buffer (pH 8.0). An 1 ml portion of the solution was centrifuged at 15000 rpm for 10 min, and the supernatant was filtered using a membrane filter having the pore size of 0.5 µm. This hGH extract solution was then subjected to size exclusion high-performance liquid chromatography under the following conditions to measure the content of hGH.
Column: TSK-gel G2000SWXL, 7.8 mm i.d.×300 mm (manufactured by Tosoh Corporation)
Mobile phase: 0.05 mol/l ammonium hydrogencarbonate solution
Flow rate: 0.6 ml/min The results are shown in Table 1.

TABLE 1

Contents of residual dichloromethane and hGH in microcapsules

| | Conditions for treatment | | | Quality | |
|---|---|---|---|---|---|
| | Pressure (Mpa) | Temperature (° C.) | Time (min) | Residual DCM (ppm) | Content of hGH (%) |
| | Untreated microcapsules | | | 738 | 10.61 |
| (1) | 2 | 15 | 15 | 137 | 10.50 |
| (2) | 2 | 15 | 30 | 50 | 10.46 |
| (3) | 2 | 15 | 45 | <32 | 10.41 |
| (4) | 2 | 15 | 60 | <32 | 10.52 |

As seen from the results in Table 1, the amount of residual dichloromethane in the microcapsules treated with carbon dioxide in a high-pressure gaseous state markedly decreased in comparison with the untreated microcapsules. Furthermore, it was found that the content of hGH in the microcapsules did not decrease by the treatment with carbon dioxide in a high-pressure gaseous state.

TEST EXAMPLE 2

For the hGH-containing microcapsules and untreated lyophilized microcapsules obtained in Example 1 (1) to (4), the amount of hGH aggregate and hGH related protein in the microcapsules were measured by the following method.

(1) hGH Aggregate

Microcapsules (10 mg) were weighted precisely, acetonitrile (2.5 ml) was added thereto, and the sample was dispersed by ultrasonic irradiation. The sample was subsequently irradiated with ultrasonic for about 2 min, and centrifuged at 3000 rpm for 10 minutes. The supernatant was removed, and acetonitrile (2.5 ml) was added to the residue. The residue was dispersed by ultrasonic irradiation. The dispersion was subsequently irradiated with ultrasonic for about 2 minutes, and centrifuged at 3000 rpm for 10 minutes. The supernatant was removed, and the residue was dried in a desiccator under reduced pressure. To the residue was added a diluent (phosphate buffer (pH 8.0)/acetonitrile mixed solution (13:7), 1.25 ml), and the sample was dispersed by ultrasonic irradiation. The dispersion was subsequently irradiated with ultrasonic for about 2 min and filtered with a membrane filter having a pore size of 0.5 μm, and the filtrate was used as a sample solution. Separately, hGH reference standard (0.2 ml) was added to a diluent (0.2 ml). This solution (0.2 ml) was added to a diluent (4.8 ml) to obtain a standardized solution. The sample solution and standardized solution (each 50 μl) were measured by liquid chromatography under the following conditions, respectively. The peak area of the peak that elutes earlier than the retention time of hGH in the sample solution and the peak area of hGH in the standardized solution were measured by automatic integration to calculate the content of aggregate. At the same time, a diluent (50 μl) was injected and the peak detected in blank was subtracted from the calculation.
Detector: ultraviolet spectrometer (wavelength for measurement: 214 nm)
Column: TSK-gel G2000SWXL, 7.8 mm i.d.×300 mm (manufactured by Tosoh Corporation)
Column temperature: constant temperature about 25° C.
Mobile phase: 0.05 mol/l ammonium hydrogencarbonate solution
Flow rate: 0.6 ml/min (2) hGH Related Protein Microcapsules (40 mg) were precisely weighed and acetonitrile (2 ml) was added thereto. The sample was dispersed by ultrasonic irradiation. The dispersion was subsequently irradiated with ultrasonic for about 2 minutes. Phosphate buffer (pH8.0, 3 ml) was added thereto and the dispersion was irradiated with ultrasonic for about 2 minutes with occasionally shaking, and centrifuged at 4° C. for 3500 rpm for 10 minutes. The supernatant was filtered with a membrane filter having pore size of 0.5 μm, and the filtrate was used as a sample solution. Separately, hGH reference standard (0.1 ml) was added to a diluent (phosphate buffer (pH 8.0)/acetonitrile mixed solution (13:7), 3.9 ml) to obtain a standardized solution. The sample solution and standardized solution (each 20 μl) were measured by liquid chromatography under the following conditions, respectively. The peak areas of the substances other than hGH in the sample solution and the peak area of hGH in the standardized solution were measured by automatic integration, respectively, to calculate the content of related protein. At the same time, a diluent (20 μl) was injected and the peak detected in blank was subtracted from the calculation.
Detector: ultraviolet spectrometer (measurement wavelength: 220 nm)
Column: PROTEIN C4, 4.6 mm i.d.×250 mm (VYDAC)
Column temperature: constant temperature about 45° C.
Mobile phase:(A) 2-amino-2-hydroxymethyl-1,3-propanediol buffer (pH 7.5)/1-propanol mixed solution (19:6)
(B) 2-amino-2-hydroxymethyl-1,3-propanediol buffer (pH 7.5)/1-propanol mixed solution (17:8)
The solution (A) and solution (B) were flowed in the proportion of (1:1).
Flow rate: 0.5 ml/min
The results are shown in Table 2.

TABLE 2

Contents of hGH aggregate and related protein in microcapsules

| | Conditions for treatment | | | Quality | |
|---|---|---|---|---|---|
| | Pressure (Mpa) | Temperature (° C.) | Time (min) | Aggregate (%) | Related protein (%) |
| | Untreated microcapsules | | | 1.95 | 5.08 |
| (1) | 2 | 15 | 15 | 2.00 | 5.42 |
| (2) | 2 | 15 | 30 | 1.96 | 5.47 |
| (3) | 2 | 15 | 45 | 1.94 | 5.50 |
| (4) | 2 | 15 | 60 | 1.95 | 5.26 |

As seen from the results in Table 2, the amounts of hGH aggregate and related protein in the microcapsules treated with carbon doixide in the state of high-pressure gas did not increase in comparison with those of the untreated microcapsules.

TEST EXAMPLE 3

For the hGH-containing microcapsules and untreated lyophilized microcapsules obtained in Example 1 (1) to (4), the mean particle diameter and in vivo initial release percentage of the microcapsules were measured by the following method.

(1) Mean Particle Diameter of Microcapsules

The mean particle diameter of microcapsules was measured using a measurement apparatus for particle size distribution (Multisizer II, Coulter Electronics Ltd., Beds, UK).

(2) In vivo Initial Release Percentage

Rats were subjected to immunosuppression treatment with tacrolimus. Prograf injection (manufactured by Fujisawa Pharmaceutical Co., Ltd., 5 mg) was diluted with saline. The dilution was subcutaneously administered at the dose of, 0.4 mg/0.2 ml/rat (three days before the first administration of the microcapsules), 0.2 mg/0.2 ml/rat (immediately after the first administration of microcapsules, and on the 4th, 7th and 11th days after administration), 0.3 mg/0.2 ml/rat (on the 14th, 18th, 21st, 25th, 28th and 32nd days after the first administration), respectively, whereby the production of antibodies to hGH could be suppressed, which allowed the evaluation of the concentration of hGH in the blood serum of rats for 5 weeks after the first administration.
The microcapsules were dispersed in a dispersion medium (5% mannitol, 0.5% carboxymethylcellulose, 0.1%

Tween80) at the concentration of 16 mg hGH/ml. The obtained dispersion (0.75 ml) was subcutaneous administered to the back of the rat under ether anesthesia. The dose was 12 mg as hGH. After the administration of the microcapsules, blood was collected with time from the caudal vein and blood serum was fractionated.

The measurement of the concentration of hGH in blood serum was measured by immunoradiometric assay (Ab beads HGH, manufactured by Eiken Chemical Co., Ltd.).

To the immunosuppressed rats were subcutaneously administered a solution of hGH at the dose of 5, 10 and 20 mg/kg, respectively, and blood was collected with time and the concentration of hGH in blood serum was measured. AUC was calculated by trapezoid method. From the AUC up to 24 hours after administration of microcapsules, the administered amount of hGH, the corresponding administered amount of hGH solution in the case of subcutaneous administration was calculated, which was divided by the administered amount of microcapsules (12 mg) to calculate the initial release percentage.

The results are shown in Table 3.

TABLE 3

Mean particle diameter and initial release percentage of microcapsules

| | Conditions for treatment | | | Quality | |
|---|---|---|---|---|---|
| | Pressure (Mpa) | Temperature (° C.) | Time (min) | Mean particle diameter (μm) | Initial release percentage (%) |
| | Untreated microcapsules | | | 36.2 | 28.3 |
| (1) | 2 | 15 | 15 | 34.9 | 17.0 |
| (2) | 2 | 15 | 30 | 35.7 | 16.7 |
| (3) | 2 | 15 | 45 | 35.1 | 13.8 |
| (4) | 2 | 15 | 60 | 37.7 | 24.2 |

As seen from the results in Table 3, it was confirmed that the mean particle diameter of the microcapsules did not change by the treatment with carbon dioxide in a high-pressure gaseous state and did not aggregate. Furthermore, the initial release percentage of the microcapsules treated with carbon dioxide in a high-pressure gaseous state markedly decreased in comparison with that of the untreated microcapsules.

TEST EXAMPLE 4

For the hGH-containing microcapsules and untreated lyophilized microcapsules obtained in Example 2 (1) to (4), the amount of residual dichloromethane (DCM) and hGH content in the microcapsules were measured by the following method.

(1) Amount of Residual Dichloromethane (DCM)

Microcapsules (about 100 mg) were weighed precisely, dissolved in dimethylsulfoxide to made up to exactly 5 ml to prepare a sample solution. Separately, dichloromethane (about 1 g) was measured precisely, and dimethylsulfoxide was added thereto to made up to exactly 20 ml. This solution was diluted by exactly 10000 times with dimethylsulfoxide to obtain a standardized solution. The sample solution and standardized solution (each 1 μl) were tested by gas chromatography under the following conditions, and the peak area of dichloromethane for each solution was measured by automatic integration to calculate the amount of dichloromethane.

Detector: hydrogen flame ionization detector
Column: OVI-G43 film thickness 3 μm, 0.53 mm i.d.×30 m (Supelco)
Inlet temperature: 140° C.
Detector temperature: 260° C.
Column temperature: 40° C. (10 min retention)→240° C. (35° C./min)→240° C. (20 min retention)→cooling→40° C.
Carrier gas: helium
Flow: 35 cm/sec (2) hGH Content Microcapsules (20 mg) were weighed precisely in a 5 ml graduated flask, and acetonitrile (1.75 ml) was added thereto and the mixture was ultra-sonicated. To the obtained acetonitrile solution was added 150 mM phosphate saline buffer (pH 8.0, 3 ml) and the solution was ultra-sonicated. To the solution was added 150 mM phosphate saline buffer (pH 8.0) to make up to a given volume. A 1 ml portion of the solution was centrifuged at 15000 rpm for 10 min, and the supernatant was filtered using a membrane filter having the pore size of 0.5 μm. This hGH extract solution was then subjected to size exclusion high-performance liquid chromatography under the following conditions to measure the content of hGH.

Column: TSK-gel G2000SWXL, 7.8 mm i.d.×300 mm (manufactured by Tosoh Corporation)
Mobile phase: 0.05 mol/l ammonium hydrogencarbonate solution
Flow rate: 0.6 ml/min The results are shown in Table 4.

TABLE 4

Contents of residual dichloromethane and hGH in microcapsules

| | Conditions for treatment | | | Quality | |
|---|---|---|---|---|---|
| | Pressure (Mpa) | Temperature (° C.) | Time (min) | Residual DCM (ppm) | Content of hGH (%) |
| | Untreated microcapsules | | | 4283 | 4.82 |
| (1) | 2 | 15 | 30 | 683 | 4.72 |
| (2) | 2 | 15 | 60 | 207 | 4.74 |
| (3) | 2 | 15 | 180 | 26 | 4.68 |
| (4) | 1 | 15 | 720 | 1000 | 4.74 |

As is seen from the results in Table 4, the amount of residual dichloromethane in the microcapsules treated with carbon dioxide in a high-pressure gaseous state markedly decreased in comparison with that of the untreated microcapsules. Furthermore, it was found that the content of hGH in the microcapsules was not decreased by the treatment with carbon dioxide in a high-pressure gaseous state.

TEST EXAMPLE 5

For the hGH-containing microcapsules and untreated lyophilized microcapsules obtained in Example 2 (1) to (4), the amount of hGH aggregate and hGH related protein in the microcapsules were measured by the following method.

(1) hGH Aggregate

Microcapsules (10 mg) were weighed precisely, acetonitrile (2.5 ml) was added thereto, and the sample was dispersed by ultrasonic irradiation. The sample was subsequently irradiated with ultrasonic for about 2 minutes, and centrifuged at 3000 rpm for 10 minutes. The supernatant was removed, and acetonitrile (2.5 ml) was added to the residue. The residue was dispersed by ultrasonic irradiation. The dispersion was subsequently irradiated with ultrasonic for about 2 min, and centrifuged at 3000 rpm for 10 minutes. The supernatant was removed, and the residue was dried in a desiccator under reduced pressure. To the residue was added a diluent (phosphate buffer (pH 8.0)/acetonitrile mixed solution (13:7), 1.25 ml), and the sample was dispersed by ultrasonic irradiation. The dispersion was subsequently irradiated with ultrasonic for about 2 minutes and filtered with a membrane filter having pore size of 0.5 μm, and the filtrate was used as a sample solution. Separately, hGH reference standard (0.2 ml) was added to a diluent (0.2 ml). This solution (0.2 ml) was added to a diluent (4.8 ml) to obtain a standardized solution. The sample solution and standardized solution (each 50 μl) were measured by liquid chromatography under the following conditions, respectively. The peak area of the peak that eluted earlier than the retention time of hGH in the sample solution and the peak area of hGH in the standardized solution were measured by automatic integration to calculate the content of aggregate. At the same time, a diluent (50 μl) was injected and the peak detected in blank was subtracted from the calculation.

Detector: ultraviolet spectrometer (wavelength for measurement: 214 nm)
Column: TSK-gel G2000SWXL, 7.8 mm i.d.×300 mm (manufactured by Tosoh Corporation)
Column temperature: constant temperature about 25° C.
Mobile phase: 0.05 mol/l ammonium hydrogencarbonate solution
Flow rate: 0.6 ml/min (2) hGH Related Protein Microcapsules (40 mg) were precisely weighed and acetonitrile (2 ml) was added thereto. The sample was dispersed by ultrasonic irradiation. The dispersion was subsequently irradiated with ultrasonic for about 2 minutes. Phosphate buffer (pH 8.0, 3 ml) was added thereto and the dispersion was irradiated with ultrasonic for about 2 minutes with occasionally shaking, and centrifuged at 4° C. for 3500 rpm for 10 min. The supernatant was filtered with a membrane filter having pore size of 0.5 μm, and the filtrate was used as a sample solution. Separately, hGH reference standard (0.1 ml) was added to a diluent (phosphate buffer (pH 8.0)/acetonitrile mixed solution (13:7), 3.9 ml) to obtain a standardized solution. The sample solution and standardized solution (each 20 μl) were measured by liquid chromatography under the following conditions, respectively. The peak areas of the substances other than hGH in the sample solution and the peak area of hGH in the standardized solution were measured by automatic integration, respectively, to calculate the content of related protein. At the same time, a diluent (20 μl) was injected and the peak detected in blank was subtracted from the calculation.

Detector: ultraviolet spectrometer (measurement wavelength: 220 nm)
Column: PROTEIN C4, 4.6 mm i.d.×250 mm (VYDAC)
Column temperature: constant temperature about 45° C.
Mobile phase: (A) 2-amino-2-hydroxymethyl-1,3-propanediol buffer (ph 7.5)/1-propanol mixed solution (19:6)
(B) 2-amino-2-hydroxymethyl-1,3-propanediol buffer (ph 7.5)/1-propanol mixed solution (17:8)
The solution (A) and solution (B) were flowed in the proportion of (1:1).
Flow rate: 0.5 ml/min The results are shown in Table 5.

TABLE 5

Contents of hGH aggregate and related protein in microcapsules

| | Conditions for treatment | | | Quality | |
|---|---|---|---|---|---|
| | Pressure (Mpa) | Temperature (° C.) | Time (min) | Aggregate (ppm) | Relalted protein (%) |
| | Untreated microcapsules | | | 1.44 | 7.46 |
| (1) | 2 | 15 | 30 | 1.29 | 7.90 |
| (2) | 2 | 15 | 60 | 1.24 | 7.44 |
| (3) | 2 | 15 | 180 | 1.38 | 7.48 |
| (4) | 1 | 15 | 720 | 1.48 | 7.54 |

As is seen from the results in Table 5, the amounts of hGH aggregate and related protein in the microcapsules treated with carbon dioxide in the high-pressure gaseous state did not increase in comparison with those of the untreated microcapsules.

TEST EXAMPLE 6

For the hGH-containing microcapsules and untreated lyophilized microcapsules obtained in Example 2 (1) to (4), the mean particle diameter and in vivo initial release percentage of the microcapsules were measured by the following method.

(1) Mean Particle Diameter of Microcapsules

The mean particle diameter of microcapsules was measured using a measurement apparatus for particle size distribution (Multisizer II, Coulter Electronics Ltd., Beds, UK).

(2) In vivo Initial Release Percentage

Rats were subjected to immunosuppression treatment with tacrolimus. Prograf injection (manufactured by Fujisawa Pharmaceutical Co., Ltd., 5 mg) was diluted with saline. The dilution was subcutaneously administered in the dose of, 0.4 mg/0.2 ml/rat (three days before administration of the microcapsules), 0.2 mg/0.2 ml/rat (immediately after the first administration of microcapsules, and on the 4th, 7th, 11th, 14th and 18th days after the first administration), respectively. The microcapsules were dispersed in a dispersion medium (5% mannitol, 0.5% carboxymethylcellulose, 0.1% Tween80) at the concentration of 8 mg hGH/ml. The obtained dispersion (0.75 ml) was subcutaneous administered to the back of the rat under ether anesthesia. The dose was 6 mg as hGH. After the administration of the microcapsules, blood was sequentially taken from the caudal vein and blood serum was fractionated.

The concentration of hGH in blood serum was measured by immunoradiometric assay (Ab beads HGH, Eiken Chemical Co., Ltd.).

To the immunosuppressed rat was subcutaneously administered a solution of hGH at the dose of 5, 10 and 20 mg/kg, respectively, and blood was collected with time and the concentration of hGH in blood serum was measured. AUC was calculated by trapezoid method. From the AUC up to 24 hr after administration of microcapsules, the administered amount of hGH, the corresponding administered amount of hGH solution in the case of subcutaneous administration was calculated, which was divided by the administered amount of microcapsules (6 mg) to calculate the initial release percentage.

The results are shown in Table 6.

TABLE 6

Mean particle diameter and initial release percentage of microcapsules

| Conditions for treatment | | | Quality | |
|---|---|---|---|---|
| Pressure (Mpa) | Temperature (° C.) | Time (min) | Mean particle diameter (μm) | Initial release percentage (%) |
| Untreated microcapsules | | | 36.6 | 25.8 |
| (1) 2 | 15 | 30 | 37.9 | 13.9 |
| (2) 2 | 15 | 60 | 37.2 | 15.0 |
| (3) 2 | 15 | 180 | 37.9 | 19.0 |
| (4) 1 | 15 | 720 | 37.3 | 14.7 |

As is seen from the results in Table 6, it was confirmed that the mean particle diameter of the microcapsules was not changed by the treatment with carbon dioxide in the high-pressure gaseous state and the microcapsules did not aggregate. Furthermore, the initial release percentage of the microcapsules treated with carbon dioxide in the high-pressure gaseous state markedly decreased in comparison with that of the untreated microcapsules.

TEST EXAMPLE 7

For the candesartan-containing microcapsules and untreated lyophilized microcapsules obtained in Example 3 (1) to (18), the amount of residual dichloromethane (DCM) and candesartan content in the microcapsules were measured by the following method.

(1) Amount of Residual Dichloromethane (DCM)

Microcapsules (about 100 mg) were weighed precisely, dissolved in dimethylsulfoxide to make up to exactly 5 ml to prepare a sample solution. Separately, dichloromethane (about 1 g) was weighed precisely, and dimethylsulfoxide was added thereto to make up to exactly 20 ml. This solution was diluted by exactly 10000 times with dimethylsulfoxide to obtain a standardized solution. The sample solution and standardized solution (each 1 μl) were tested by gas chromatography under the following conditions, and the peak area of dichloromethane for each solution was measured by automatic integration to calculate the amount of dichloromethane.

Detector: hydrogen flame ionization detector
Column: OVI-G43 film thickness 3 μm, 0.53 mm i.d.×30 m (Supelco)
Inlet temperature: 140° C.
Detector temperature: 260° C.
Column temperature: 40° C. (10 min retention)→260° C. (35° C./min) (10 min retention)
Carrier gas: helium
Flow: 35 cm/sec (2) Candesartan Content Microcapsules (5 to 10 mg) were weighed precisely in a centrifuge tube, HPLC mobile phase (30 ml) was added thereto and the mixture was stirred with shaking for 1 hour. The mixture was then centrifuged at 2950 rpm for 10 minutes, and the supernatant was filtered with a membrane filter having the pore size of 0.5 μm. This candesartan extract solution was then subjected to reverse phase high-performance liquid chromatography under the following conditions to measure the content of candesartan.

Column: Inertsil ODS-3 (4.6 mm×150 mm, manufactured by GL science)
Mobile phase: 0.1M $KH_2PO_4$/AcCN/MeOH/AcOH=50/35/15/1 (v/v)
Flow rate: 1 ml/min
Detection: UV wavelength 254 nm The results are shown in Table 7.

TABLE 7

Contents of residual dichloromethane and candesartan in microcapsules

| Conditions for treatment | | | | Quality | |
|---|---|---|---|---|---|
| Pressure (Mpa) | Temperature (° C.) | Time (min) | Charged amount (g) | Residual dichloromethane (ppm) | Drug content (%) |
| Untreated microcapsules | | | | 18026 | 26.5 |
| (1) 2.0 | 15 | 30 | 0.3 | 826 | 26.0 |
| (2) 2.0 | 15 | 60 | 0.3 | 230 | 26.0 |
| (3) 2.0 | 15 | 120 | 0.3 | 106 | 26.5 |
| (4) 2.0 | 15 | 180 | 0.3 | 0 | 26.3 |
| (5) 2.5 | 15 | 30 | 0.3 | 411 | 26.1 |
| (6) 2.5 | 15 | 60 | 0.3 | 375 | 26.9 |
| (7) 2.5 | 15 | 120 | 0.3 | 0 | 26.9 |
| (8) 2.5 | 15 | 180 | 0.3 | 0 | 26.5 |
| (9) 3.0 | 15 | 15 | 0.3 | 6923 | 26.8 |
| (10) 3.0 | 15 | 30 | 0.3 | 2993 | 26.2 |
| (11) 3.0 | 15 | 60 | 0.3 | 0 | 26.8 |
| (12) 3.0 | 15 | 120 | 0.3 | 0 | 26.9 |
| (13) 3.0 | 15 | 180 | 0.3 | 0 | 26.8 |
| (14) 3.5 | 15 | 30 | 0.3 | 3926 | 26.3 |
| (15) 3.5 | 15 | 60 | 0.3 | 0 | 27.1 |
| (16) 3.5 | 15 | 120 | 0.3 | 321 | 26.9 |
| (17) 3.5 | 15 | 180 | 0.3 | 0 | 26.5 |
| (18) 4.0 | 15 | 30 | 0.3 | 1148 | 27.1 |

As is seen from the results in Table 7, the amount of residual dichloromethane in the microcapsules treated with carbon dioxide in the high-pressure gaseous state markedly decreased in comparison with that of the untreated microcapsules. Furthermore, it was confirmed that the content of candesartan in the microcapsules was not decreased by the treatment with carbon dioxide in the state of high-pressure gas.

TEST EXAMPLE 8

For the candesartan-containing microcapsules and untreated lyophilized microcapsules obtained in Example 4 (1) to (3), the amount of residual dichloromethane (DCM)

and candesartan content in the microcapsules were measured by the similar method to that of Test Example 7.

The results are shown in Table 8.

TABLE 8

Contents of residual dichloromethane and candesartan in microcapsules

| | Conditions for treatment | | | | Quality | |
|---|---|---|---|---|---|---|
| | | | | | Residual | |
| | Pressure (Mpa) | Temperature (° C.) | Time (min) | Charged amount (g) | dichloromethane (ppm) | Drug content (%) |
| | Untreated microcapsules | | | | 24692 | 26.4 |
| (1) | 3.0 | 15 | 60 | 0.3 | 116 | 26.8 |
| (2) | 3.0 | 15 | 60 | 2 | 0 | 26.4 |
| (3) | 3.0 | 15 | 60 | 5 | 137 | 27.7 |

As is seen from the results in Table 8, the amount of residual dichloromethane in the microcapsules treated with carbon dioxide in the high-pressure gaseous state markedly decreased in comparison with that of the untreated microcapsules. Furthermore, it was confirmed that the content of candesartan in the microcapsules did not decrease by the treatment with carbon dioxide in a high-pressure gaseous state.

INDUSTRIAL APPLICABILITY

According to the present invention, in a method for producing a sustained-release preparation, by forming a solid material containing a bioactive substance and a polymer and contacting the solid material with high-pressure gas, it is possible to produce a sustained-release preparation which is a medicament having such very superior clinical properties that the excess amount of initial release of the bioactive substance immediately after administration is markedly suppressed, a constant amount of the bioactive substance is being released from immediately after administration over a long period of time, and the denaturation of the bioactive substance and the residual organic solvent are extremely decreased. Furthermore, by modifying the method for removing a solvent, the treatment period required for the removal of the solvent has been markedly decreased.

The invention claimed is:

1. A method for producing sustained-release microcapsules containing a non-peptidic bioactive substance, which comprises forming a solid material containing the non-peptidic bioactive substance and a polymer by (a) in-water drying method, (b) phase separation method or (c) spray-drying method, and then contacting the solid material with carbon dioxide to form the sustained-release microcapsules, wherein the pressure of the carbon dioxide is 1 MPa to 7 MPa at a temperature range of −60° C. to +20° C. based on the glass transition temperature of the polymer, with the proviso that the solid material is not in contact with the carbon dioxide before or during formation of the solid material.

2. The method according to claim 1, wherein the non-peptidic bioactive substance is unstable to heat or solvents.

3. The method according to claim 1, wherein the non-peptidic compound is a compound having an oxygen atom in the molecule.

4. The method according to claim 1, wherein the non-peptidic compound is a compound having an ether bond or a carbonyl group.

5. The method according to claim 1, wherein the non-peptidic compound is a compound represented by the formula (I):

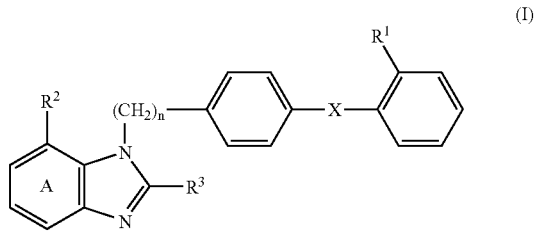

wherein $R^1$ represents a group capable of forming an anion or a group which may be converted into said group, X represents that the phenylene group and the phenyl group are linked directly or via a spacer of an atomic chain having two or less atom(s), n represents an integer of 1 or 2, ring A represents a benzene ring which may be further substituted, $R^2$ represents a group capable of forming an anion or a group which may be converted into said group, $R^3$ represents a hydrocarbon residue which may link via a heteroatom and may be substituted, or a salt thereof.

6. The method according to claim 1, wherein the non-peptidic compound is losartan, eprosartan, candesartan cilexetil, candesartan, valsartan, telmisartan, irbesartan, tasosartan or olmesartan.

7. The method according to claim 1, wherein the non-peptidic compound is candesartan.

8. The method according to claim 1, wherein the polymer is biodegradable.

9. The method according to claim 8, wherein the biodegradable polymer is a homopolymer or a copolymer of α-hydroxycarboxylic acids, or a mixture thereof.

10. The method according to claim 9, wherein the biodegradable polymer is a homopolymer or a copolymer of lactic acid/glycolic acid having a composition ratio of lactic acid/glycolic acid of 100/0 to 40/60 mol %.

11. The method according to claim 9, wherein the biodegradable polymer is a homopolymer of lactic acid.

12. The method according to claim 8, wherein the weight-average molecular weight of the biodegradable polymer is 3,000 to 50,000.

13. The method according to claim 1, wherein the solid material is contacted with carbon dioxide, wherein the pressure of the carbon dioxide is 1 MPa to 7 MPa at a temperature range of −40° C. to +0° C. based on the glass transition temperature of the polymer.

14. The method according to claim 1, wherein the period for contacting the solid material with carbon dioxide is 5 minutes to 48 hours.

15. The method according to claim 14, wherein the period for contacting the solid material with carbon dioxide is 10 minutes to 12 hours.

16. The method according to claim 1, wherein the carbon dioxide is inert to the non-peptidic bioactive substance and polymer.

17. The method according to claim 1, wherein the pressure of the carbon dioxide is 1 MPa to 4 MPa.

18. The method according to claim 1, wherein the solid material is obtained by in-water drying method.

* * * * *